US010687788B2

(12) United States Patent
Kang et al.

(10) Patent No.: US 10,687,788 B2
(45) Date of Patent: Jun. 23, 2020

(54) IMAGE PROCESSING APPARATUS, CONTROL METHOD THEREOF, AND ULTRASOUND IMAGING APPARATUS

(71) Applicant: SAMSUNG ELECTRONICS CO., LTD., Suwon-si (KR)

(72) Inventors: Jooyoung Kang, Yongin-si (KR); Sungchan Park, Suwon-si (KR); Baehyung Kim, Yongin-si (KR); Jungho Kim, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 626 days.

(21) Appl. No.: 14/827,649

(22) Filed: Aug. 17, 2015

(65) Prior Publication Data

US 2016/0128675 A1    May 12, 2016

(30) Foreign Application Priority Data

Nov. 12, 2014 (KR) .................. 10-2014-0157126

(51) Int. Cl.
*A61B 8/08* (2006.01)
*A61B 8/14* (2006.01)
*G01S 15/89* (2006.01)
*A61B 8/00* (2006.01)
*G01S 7/52* (2006.01)

(52) U.S. Cl.
CPC .......... *A61B 8/5207* (2013.01); *A61B 8/0833* (2013.01); *A61B 8/463* (2013.01); *A61B 8/481* (2013.01); *A61B 8/488* (2013.01); *A61B 8/5223* (2013.01); *A61B 8/5246* (2013.01); *G01S 7/52038* (2013.01); *G01S 7/52047* (2013.01); *G01S 15/8977* (2013.01); *A61B 8/469* (2013.01); *G01S 7/52049* (2013.01)

(58) Field of Classification Search
CPC ... A61B 8/5207; A61B 8/5246; A61B 8/5223; A61B 8/0833; A61B 8/463; A61B 8/481; A61B 8/488; G01S 7/52038; G01S 7/52047; G01S 7/52049; G01S 15/8977
See application file for complete search history.

(56) References Cited

U.S. PATENT DOCUMENTS

| 5,924,991 A * | 7/1999 | Hossack ................ A61B 8/14 |
| | | 128/916 |
| 5,970,025 A * | 10/1999 | Cole .................... G01S 7/5202 |
| | | 367/11 |
| 6,454,715 B2 * | 9/2002 | Teo ........................ A61B 8/06 |
| | | 600/443 |

(Continued)

OTHER PUBLICATIONS

Shung, Diagnostic Ultrasound: Imaging and Blood Flow Measurements. Published 2006 by Taylor & Francis Group.*

*Primary Examiner* — Pascal M Bui Pho
*Assistant Examiner* — Colin T. Sakamoto
(74) *Attorney, Agent, or Firm* — Sughrue Mion, PLLC

(57) ABSTRACT

An image processing apparatus includes a speckle energy analyzer configured to analyze speckle energy of an ultrasound image signal, the ultrasound image signal being received from an ultrasound probe, and an image decomposer configured to decompose the ultrasound image signal into one or more ultrasound image signals of different frequency bands, based on the analyzed speckle energy of the ultrasound image signal.

15 Claims, 18 Drawing Sheets

(56) References Cited

U.S. PATENT DOCUMENTS

| | | | | |
|---|---|---|---|---|
| 6,704,437 B1* | 3/2004 | He | ............................ | G06T 5/20 |
| | | | | 382/128 |
| 2004/0054281 A1* | 3/2004 | Adam | ..................... | A61B 8/587 |
| | | | | 600/437 |
| 2007/0083114 A1* | 4/2007 | Yang | ........................ | A61B 8/00 |
| | | | | 600/437 |
| 2009/0209858 A1* | 8/2009 | Oelze | .................. | G01S 7/52077 |
| | | | | 600/443 |
| 2011/0090371 A1* | 4/2011 | Cote | ................... | H04N 5/2176 |
| | | | | 348/237 |
| 2014/0066768 A1* | 3/2014 | Sui | ...................... | G01S 7/52038 |
| | | | | 600/443 |
| 2014/0276065 A1* | 9/2014 | He | ......................... | A61B 8/5207 |
| | | | | 600/445 |
| 2016/0199030 A1* | 7/2016 | Patil | ......................... | B06B 1/02 |
| | | | | 600/459 |

* cited by examiner

ANALYSIS OF SPECKLE ENERGY BASED ON DEPTH

ANALYSIS OF SPECKLE ENERGY BASED ON IMAGES AFTER DECOMPOSITION

IMAGE PROCESSING APPARATUS, CONTROL METHOD THEREOF, AND ULTRASOUND IMAGING APPARATUS

CROSS-REFERENCE TO RELATED APPLICATION

This application claims priority from Korean Patent Application No. 10-2014-0157126, filed on Nov. 12, 2014, in the Korean Intellectual Property Office, the disclosure of which is incorporated herein in its entirety by reference.

BACKGROUND

1. Field

Apparatuses and methods consistent with exemplary embodiments relate to an image processing apparatus of restoring images through frequency decomposition and compounding, a control method of the image processing apparatus, and an ultrasound imaging apparatus, and more particularly to, a technique for determining one or more frequency bands of an ultrasound image signal through analysis of speckle energy of the ultrasound image signal, acquiring adaptive multi-frequency images according to images or depths through frequency decomposition, and performing frequency compounding and axial restoration, to prevent axial resolution degradation.

2. Description of the Related Art

An ultrasound imaging apparatus is widely used for medical purposes such as, for example, observing the inside of an object, detecting foreign materials from the object, and examining an injury, by irradiating ultrasonic waves generated from transducers of a probe toward a target inside the object from the surface of the object, and receiving information of ultrasonic signals (that is, ultrasonic echo signals) reflected from the target so as to non-invasively acquire section images about soft tissue of the object or images about blood vessels of the object based on the ultrasonic echo signals.

The ultrasonic imaging apparatus has advantages in that the ultrasonic imaging apparatus is a compact, low-priced apparatus compared to other medical imaging apparatuses, such an X-ray imaging apparatus, a computed tomography (CT) scanner, a magnetic resonance image (MRI) apparatus, and a nuclear medicine diagnosis apparatus, and the ultrasonic imaging apparatus can display images in real time. Also, the ultrasonic imaging apparatus has high safety since there is no risk for patients to be exposed to radiation. For the advantages, the ultrasonic imaging apparatus is widely used.

Lately, according to the wide use of ultrasound system, requirements for ultrasound images that are provided by the ultrasound system are increasing. Particularly, since a patient's lesions or tissue needs to be accurately observed for examination, a biopsy, or a surgery, the ultrasound system needs to acquire accurate ultrasound images.

The ultrasound imaging apparatus uses a probe which is an ultrasonic wave generator in order to acquire an ultrasound image of an object. The probe includes one or more transducers such that the individual transducers transmit ultrasonic waves to an object, and receive echo ultrasonic waves from the object. In order to compensate for the differences between times of arrival of ultrasonic waves at the transducers, beamforming is performed. The ultrasound imaging apparatus acquires an ultrasound image of the object based on the beamformed signals.

In order to improve a contrast to noise ratio (CNR) of an ultrasound image, a frequency compounding method is widely used. According to the frequency compounding method, when the ultrasound imaging system extracts frequency bands in a frequency domain using beamformed images to acquire a plurality of images for the individual frequency bands, axial resolution may be degraded upon compounding of the images of narrow bands since the images have different speckle patterns due to the differences between frequency areas.

Thus, a technique for removing speckle noise caused by compounding of ultrasound images and improving resolution by analyzing speckle energy of input images is needed.

SUMMARY

One or more exemplary embodiments provide an ultrasound imaging apparatus for determining one or more frequency bands of an ultrasound image signal through analysis of speckle energy of the ultrasound image signal, acquiring adaptive multi-frequency images according to images or depths through frequency decomposition, and performing frequency compounding and axial restoration, thereby preventing axial resolution degradation, and a control method of the ultrasound imaging apparatus.

Additional aspects of the disclosure will be set forth in part in the description which follows and, in part, will be obvious from the description, or may be learned by practice of the disclosure.

In accordance with an aspect of an exemplary embodiment, an image processing apparatus includes a speckle energy analyzer configured to analyze speckle energy of an ultrasound image signal, the ultrasound image signal being received from an ultrasound probe; and an image decomposer configured to decompose the ultrasound image signal into one or more ultrasound image signals of different frequency bands, based on the analyzed speckle energy of the ultrasound image signal.

The speckle energy analyzer may analyze the speckle energy of the ultrasound image signal according to a depth of the ultrasound image signal.

The speckle energy analyzer may analyze speckle energy of the one or more ultrasound image signals of the different frequency bands.

The speckle energy analyzer may obtain a speckle energy value based on a difference between a pixel value of a speckle included in the ultrasound image signal and a pixel value of an area adjacent to the speckle, and compare the speckle energy value to a predetermined speckle energy value to determine higher speckle energy or lower speckle energy.

The speckle energy analyzer may determine a lower frequency band of the ultrasound image signal in response to higher speckle energy analyzed at a first depth of the ultrasound image signal, and determine a higher frequency band of the ultrasound image signal in response to lower speckle energy analyzed at a second depth of the ultrasound image signal.

The speckle energy analyzer may determine a lower frequency band of the ultrasound image signal in response to higher speckle energy analyzed from the one or more ultrasound image signals, and determine a higher frequency band of the ultrasound image signal in response to lower speckle energy analyzed from the one or more ultrasound image signals.

The image processing apparatus may further include a filter configured to pass the ultrasound image signal of the determined frequency band, wherein the image decomposer is configured to decompose the passed ultrasound image signal into the one or more ultrasound image signals of the different frequency bands.

The image processing apparatus may further include an image compounder configured to compound the one or more ultrasound image signals of the different frequency bands into a compounded ultrasound image signal.

The image compounder may compound the one or more ultrasound image signals of the different frequency bands, based on analysis of speckle energy of the one or more ultrasound image signals of the different frequency bands.

The image processing apparatus may further include an image restorer configured to restore an axial image based on the compounded ultrasound image signal.

The image restorer may include a point spread function (PSF) estimator configured to estimate a PSF of the compounded ultrasound image signal; and a deconvolver configured to deconvolve the estimated PSF with the compounded ultrasound image signal to generate a restored image.

In accordance with an aspect of another exemplary embodiment, a method of controlling an image processing apparatus includes: analyzing speckle energy of an ultrasound image signal, the ultrasound image signal being received from an ultrasound probe; and decomposing the ultrasound image signal into one or more ultrasound image signals of different frequency bands, based on the analyzed speckle energy of the ultrasound image signal.

The analyzing may include analyzing the speckle energy of the ultrasound image signal according to a depth of the ultrasound image signal.

The analyzing may include analyzing speckle energy of the one or more ultrasound image signals of the different frequency bands.

The analyzing the speckle energy of the ultrasound image signal according to the depth of the ultrasound image signal may include determining a lower frequency band of the ultrasound image signal in response to higher speckle energy analyzed at a first depth of the ultrasound image signal, and determining a higher frequency band of the ultrasound image signal in response to lower speckle energy analyzed at a second depth of the ultrasound image signal.

The analyzing the speckle energy of the one or more ultrasound image signals of the different frequency bands may include determining a lower frequency band of the one or more ultrasound image signals in response to higher speckle energy analyzed from the one or more ultrasound image signals, and determining a higher frequency band of the one or more ultrasound image signals in response to lower speckle energy analyzed from the one or more ultrasound image signals.

The method may further include passing the ultrasound image signal of the determined frequency band; and decomposing the passed ultrasound image signal into the one or more ultrasound image signals of the different frequency bands.

The method may further include compounding the one or more ultrasound image signals of the different frequency bands into a compounded ultrasound image signal.

The method may further include restoring an axial image based on the compounded ultrasound image signal.

In accordance with an aspect of still another exemplary embodiment, an ultrasound imaging apparatus includes: an ultrasound probe configured to receive echo ultrasonic waves reflected from an object, and to convert the reflected echo ultrasonic waves into an ultrasound image signal; and an image processing apparatus configured to analyze speckle energy of the ultrasound image signal, and decompose the ultrasound image signal into one or more ultrasound image signals of different frequency bands based on the analyzed speckle energy of the ultrasound image signal.

BRIEF DESCRIPTION OF THE DRAWINGS

The above and/or other aspects will become more apparent by describing certain exemplary embodiments with reference to the accompanying drawings.

DETAILED DESCRIPTION

Figure 1:
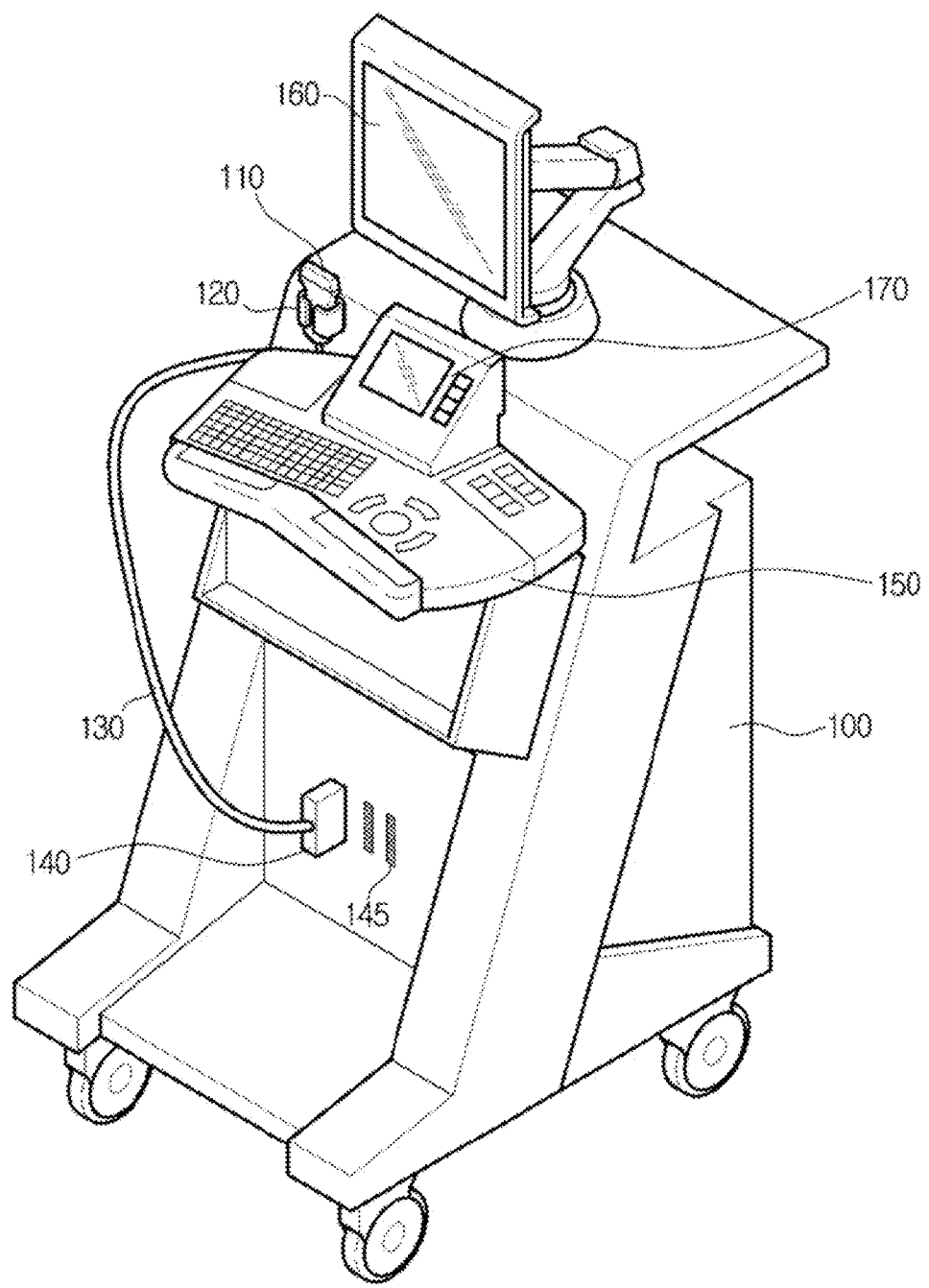
FIG. 1 is a perspective view of an ultrasound imaging apparatus according to an exemplary embodiment.

Exemplary embodiments are described in greater detail with reference to the accompanying drawings.

In the following description, the same drawing reference numerals are used for the same elements even in different drawings. The matters defined in the description, such as detailed construction and elements, are provided to assist in a comprehensive understanding of the exemplary embodiments. Thus, it is apparent that the exemplary embodiments can be carried out without those specifically defined matters. Also, well-known functions or constructions are not described in detail since they may obscure the exemplary embodiments with unnecessary detail.

Hereinafter, an image processing apparatus, a control method of the image processing apparatus, and an ultrasound imaging apparatus, according to exemplary embodiments will be described in detail with reference to the accompanying drawings. Like numbers refer to like elements throughout the description of the drawings.

A medical imaging apparatus according to an exemplary embodiment may be one of an X-ray imaging apparatus, fluoroscopy, a computed tomography (CT) scanner, a magnetic resonance image (MRI) apparatus, positron emission tomography (PET), and an ultrasound imaging apparatus. In the following description, for convenience of description, the medical imaging apparatus is assumed to be an ultrasound imaging apparatus. Also, in the following description, an "ultrasound image" means an image of an object acquired using ultrasonic waves. Also, the "object" means a human body, a fetus, an animal, a metal, a nonmetal, or a part thereof. For example, the object may include vessels or organs, such as a liver, a heart, a uterus, a brain, a breast, an abdomen, etc. Also, the object may include a phantom, and the phantom means a material having a volume that is very close to an effective atomic number and a density of a living body.

Also, in the following description, a "user" may be a medical professional, such as a doctor, a nurse, a medical technologist, a medical imaging professional, or an ultrasonographist, or may be a technician that repairs medical equipment, but not limited thereto.

FIG. 1 is a perspective view of an ultrasound imaging apparatus according to an exemplary embodiment. Referring to FIG. 1, the ultrasound imaging apparatus may include a main body 100, an ultrasound probe 110, an input unit 150, and a display 160.

In one side of the main body 100, one or more female connectors 145 may be provided. A male connector 140 connected to a cable 130 may be physically coupled with one of the female connectors 145.

At the bottom of the main body 100, a plurality of castors (not shown) may be provided to move the ultrasound imaging apparatus. The plurality of castors may fix the ultrasound imaging apparatus at a specific location or move the ultrasound imaging apparatus in a specific direction. The ultrasound imaging apparatus having the above configuration is called a cart-type ultrasound imaging apparatus.

However, the ultrasound imaging apparatus may be a portable ultrasound imaging apparatus that can be possessed by a user even when the user moves a long distance. The portable ultrasound imaging apparatus may not include castors. Examples of such a portable ultrasound imaging apparatus include a picture archiving and communication system (PACS) viewer, a smart phone, a laptop computer, a personal digital assistant (PDA), and a tablet personal computer (PC), although not limited to these.

The ultrasound probe 110 may contact the surface of an object to transmit and receive ultrasonic waves. More specifically, the ultrasound probe 110 may transmit ultrasonic waves to the inside of an object according to a transmission signal received from the main body 100, receive echo ultrasonic waves reflected from a specific part inside the object, and then transfer the received echo ultrasonic waves to the main body 100.

The ultrasound probe 110 may be connected to one end of the cable 130, and the other end of the cable 130 may be connected to the male connector 140. The male connector 140 connected to the other end of the cable 130 may be physically coupled with the female connector 145 of the main body 100.

Alternatively, the ultrasound probe 110 may be connected to the main body 100 in a wireless fashion. In this case, the ultrasound probe 110 may transmit echo ultrasonic waves received from an object to the main body 100 in the wireless fashion. Also, a plurality of ultrasound probes may be connected to the main body 100.

In the main body 100, an image processing apparatus 350 (see FIG. 2) for converting echo ultrasonic waves received from the ultrasound probe 110 into an ultrasound image may be provided. The image processing apparatus 350 may be implemented in the form of hardware such as a microprocessor, or in the form of software that can be executed on hardware.

The image processing apparatus 350 may perform scan conversion on echo ultrasonic waves to create an ultrasound image.

Also, the image processing apparatus may perform volume rendering on volume data acquired using echo ultrasonic waves to create a three dimensional (3D) ultrasound image, or create an elastic image resulting from imaging a degree of deformation of an object according to pressure applied thereto. In addition, the image processing apparatus may represent various additional information in the form of text or graphic images on the ultrasound image.

The ultrasound image may be stored in the main body 100 or in an external memory. Alternatively, the ultrasound image may be stored in a web storage or a cloud server that performs a storage function on the web.

The input unit 150 is used to receive commands related to operations of the ultrasound imaging apparatus. For example, the input unit 150 may receive a mode selection command for selecting a mode, such as an A mode, a B mode, a M mode, or a Doppler mode. Also, the input unit 150 may receive a diagnosis start command.

A command input through the input unit 150 may be transmitted to the main body 100 through wired/wireless communication.

The input unit 150 may include at least one of a keyboard, a foot switch, and a foot pedal.

For example, the keyboard may be implemented in hardware, and mounted on the upper part of the main body 100. The keyboard may include at least one(s) of a switch(s), a key(s), a joystick, and a trackball. As another example, the keyboard may be implemented as software such as a graphic user interface (GUI). The foot switch or the foot pedal may be disposed below the main body 100. The user may control a part of functions of the ultrasound imaging apparatus using the foot pedal.

The display 160 may be provided in the main body 100. The display 160 may display an ultrasound image acquired during ultrasonic diagnosis according to a command input through the input unit 150. The display 160 may be implemented as a cathode ray tube (CRT) or a liquid crystal display (LCD). FIG. 1 shows a case in which the display 160 is coupled with the main body 100, however, the display 160 may be detachably coupled with the main body 100.

The ultrasound imaging apparatus may further include a communicator. The communicator may connect to a network in a wired/wireless fashion to communicate with an external device or a server. The communicator may receive/transmit data from/to a hospital server or other medical apparatuses in a hospital, connected through PACS. Also, the communicator may perform data communication according to a digital imaging and communications in medicine (DICOM) standard.

The communicator may transmit/receive data related to diagnosis of an object, such as an ultrasound image, echo ultrasonic waves, and Doppler data of the object, through the network. Also, the communicator may transmit/receive medical images photographed by another medical apparatus, such as a CT scanner, an MRI apparatus, an X-ray apparatus, etc., through the network. In addition, the communicator may receive information about a patient's diagnosis history, therapeutic schedule, etc., from a server, and use the information for diagnosis of an object. Furthermore, the communicator may perform data communication with a doctor's or patient's mobile terminal, as well as a server or a medical apparatus in a hospital.

The communicator may connect to the network in a wired/wireless fashion to receive/transmit data from/to a server, a medical apparatus, or a mobile terminal. The communicator may include one or more components to enable communications with external devices, and may include a short-range communication module, a wired communication module, and a mobile communication module.

The short-range communication module may be a module for short-range communication within a predetermined distance. The short-range communication may be wireless local area network (WLAN), Wireless-Fidelity (Wi-Fi), Bluetooth, Zigbee, Wi-Fi Direct (WFD), Ultra Wideband (UWB), infrared data association (IrDA), Bluetooth low energy (BLE), or near field communication (NFC), although the short-range communication is not limited to these.

The wired communication module may be a module for communication based on electrical signals or optical signals, and may be a pair cable, a coaxial cable, an optical fiber cable, or an Ethernet cable.

The mobile communication module may transmit/receive radio signals from/to at least one of a base station, an external terminal, and a server over a mobile communication network. Herein, the radio signals may include voice call signals, video call signals, or various kinds of data according to text/multimedia message transmission/reception.

Figure 2:
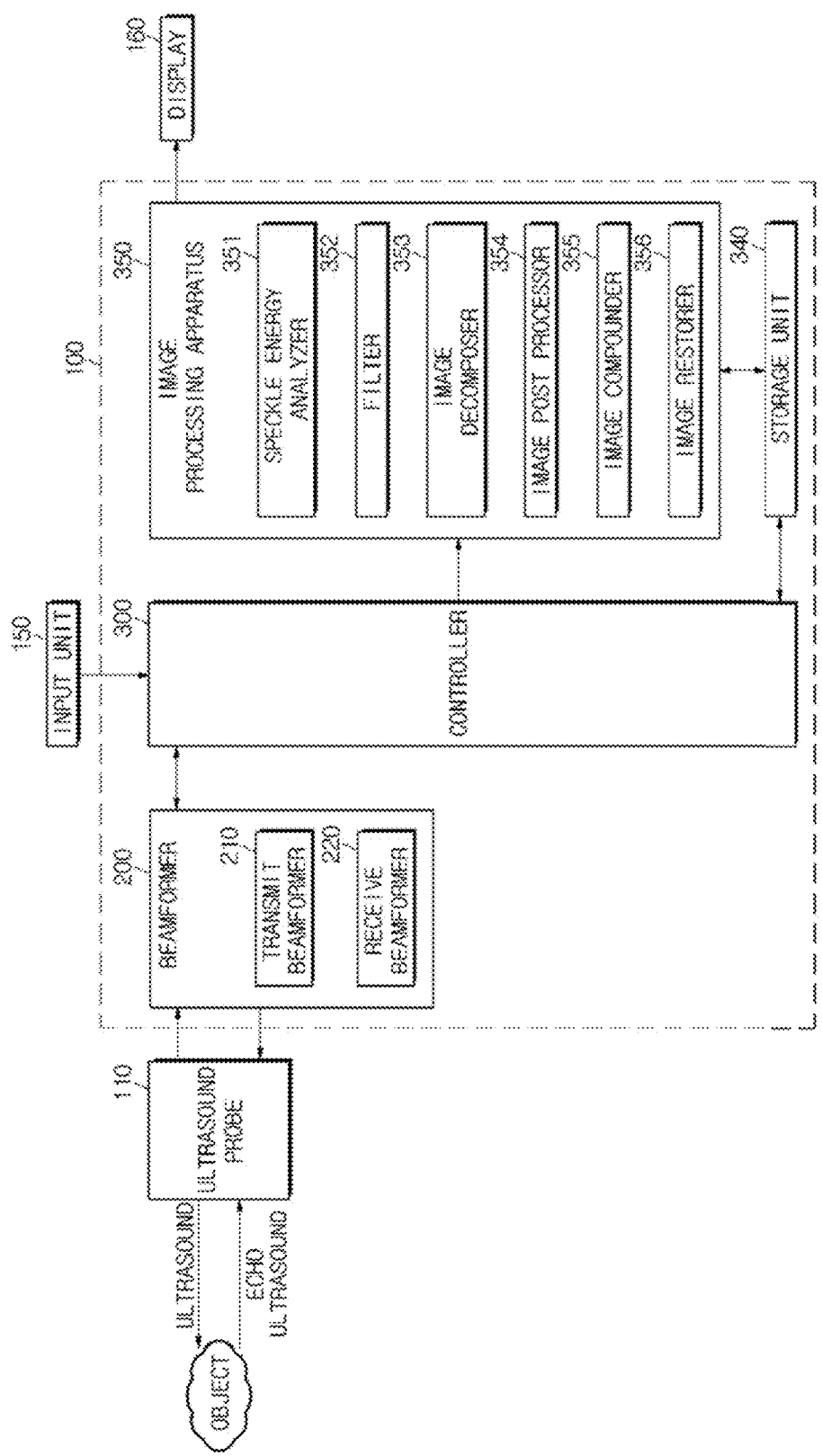
FIG. 2 is a control block diagram illustrating an image processing apparatus and an ultrasound imaging apparatus including the image processing apparatus, according to an exemplary embodiment.

FIG. 2 is a control block diagram illustrating an image processing apparatus and an ultrasound imaging apparatus including the image processing apparatus, according to an exemplary embodiments.

The ultrasound probe 110 may include a plurality of transducer elements to convert electrical signals into ultrasonic signals and vice versa. The ultrasound probe 110 may transmit ultrasonic signals to an object, and receive echo signals reflected from the object. Since ultrasonic waves are reflected with different degrees of reflectance according to medium, the ultrasound probe 110 may acquire information about the inside of an object by collecting echo ultrasonic waves reflected from the object.

The ultrasound probe 110 may be implemented in various ways within the technical concept of acquiring volume data of an object. For example, if the transducer elements of the ultrasound probe 110 has a one dimensional (1D) arrangement, the ultrasound probe 110 may acquire volume data according to a freehand method. Also, the ultrasound probe 110 may acquire volume data according to a mechanical method, without a user's manipulation. If the transducer elements of the ultrasound probe 110 has a two dimensional (2D) arrangement, the ultrasound probe 110 may acquire volume data by controlling the transducer elements.

More specifically, if the ultrasound probe 110 receives current from an external power source or an internal power source (for example, a battery), a plurality of transducer elements vibrate to generate ultrasonic signals, and the ultrasonic signals are irradiated to an external object. Then, echo signals reflected from the object are received by the plurality of transducer elements, and the plurality of transducer elements vibrate according to the received echo signals to generate current of a frequency corresponding to the vibration frequency.

Referring to FIG. 2, the main body 100 may include a beamformer 200, a controller 300, a storage unit 340, and the image processing apparatus 350.

The beamformer 200 may include a transmit beamformer 210 and a receive beamformer 220 to convert analog signals into digital signals and vice versa and to adjust time differences between ultrasonic waves that are transmitted from or received by one or more transducers.

Generally, a probe of an ultrasound imaging apparatus may be configured with one or more transducers. If ultrasonic waves in the range of several KHz to hundreds of MHz generated from the probe of the ultrasound imaging apparatus are transferred to a specific region inside a patient's body, a part of the ultrasonic waves is reflected from the layers between various tissues of the specific region. Particularly, the ultrasonic waves are reflected from regions with different densities in the body, for example, from blood cells in blood plasma, structures in organs, etc. The reflected ultrasonic waves vibrate the transducers of the probe, and the transducers output electrical pulses according to the vibrations. The electrical pulses are converted into an image. However, since the reflected ultrasonic signals have very low intensity and a low signal to noise ratio (SNR), a technique of improving the intensity and an SNR of reflected ultrasonic signals is needed in order to convert the reflected ultrasonic signals into image information. An example of the technique is beamforming.

Herein, beamforming is a technique of increasing the intensity of a signal through superposition when signals are transmitted or received using a plurality of transducers. The concept of transmit/receive beamforming using transducers with a 1D arrangement is as follows. If a point from which image information is to be acquired is a focal point, there are differences in distance between a plurality of transducers and a focal point since the transducers are aligned in a line. Accordingly, the transducers that have transmitted signals may receive reflected signals at different times, and if the received signals overlap each other, a phase mismatch occurs so that the signals cannot be amplified. That is, in beamforming, the phases of the signals need to be matched with each other.

In order to match the phases of signals, a method of delaying transmission and reception signals is used. Accordingly, beamforming methods can be classified according to methods of delaying transmission and reception signals. The beamforming methods may be classified into an analog beamforming method and a digital beamforming method. The analog beamforming method is delaying signals using a circuit device, and the digital beamforming method is delaying signals by digitalizing and storing the signals and then reading data after a predetermined time period has elapsed.

Also, the beamformer 200 may apply time delays to digital signals in consideration of the locations of vibrating transducers and a focal point, in order to compensate for differences between times at which ultrasonic waves arrive at the focal point or differences between times at which ultrasonic waves arrive at the transducers from the focal point.

That is, if a process of concentrating ultrasonic signals emitted from a plurality of transducers at a focal point is referred to as "focusing", the beamformer 200 may perform "transmit focusing" on emitted ultrasonic signals in order to compensate for differences between times at which ultrasonic signals generated from the individual transducers arrive at a focal point, and perform "receive focusing" of aligning echo signals at appropriates time intervals in order to compensate for differences between times at which echo signals arrive at the individual transducers.

The beamformer 200 may be included in the main body 100, as shown in FIG. 2, or may be included in the ultrasound probe 110.

The image processing apparatus 350 may include a speckle energy analyzer 351, a filter 352, an image decomposer 353, an image post processor 354, an image compounder 355, and an image restorer 356.

The image processing apparatus 350 may create an ultrasound image of an object using volume data of the object. The image processing apparatus 350 may create a 3D ultrasound image about a section of the object, as well as a 2D ultrasound image about the section of the object.

In order to create a 3D ultrasound image, the image processing apparatus 350 may perform volume rendering on volume data. At this time, the image processing apparatus 350 may perform volume rending on volume data using one of volume rendering methods well-known in the art.

Also, the image processing apparatus 350 may extract a target based on volume data.

The image processing apparatus 350 may be implemented in various ways within the technical concept of extracting a target inside an object based on volume data. For example, the image processing apparatus 350 may extract, as a target, a volume data region having brightness values that are within a predetermined range. Also, the image processing apparatus 350 may extract a target by determining whether or not the size of a volume data region having predetermined brightness values is within a predetermined range.

The image processing apparatus 350 may include the speckle energy analyzer 351 to analyze ultrasonic speckle energy based on beamformed image signals.

Also, the image processing apparatus 350 may include the filter 352 and the image decomposer 353, wherein the filter 352 passes the image signals according to the frequency bands of the image signals determined based on the analyzed speckle energy, and the image decomposer 353 decomposes the image signals passed through the filter 352 into one or more image signals of different frequency bands. The image post processor 354 may perform post processing including envelop detection and log compression. The image compounder 355 may compound the decomposed image signals. The image restorer 356 may create a restored image for the decomposed image signals.

The above described elements including the speckle energy analyzer 351 to the image restorer 356 will be described in detail below with reference to FIGS. 2 and 9.

As shown in FIG. 2, the storage unit 340 may store data or algorithms for controlling the ultrasound imaging apparatus.

The storage unit 340 may store image data of resultant images created by the image processing apparatus 350, and store speckle energy data that is used as comparison data in order to analyze speckle energy of image signals. The speckle energy data may be input and stored by a user. According to an exemplary embodiment, analyzed speckle energy of image signals may be automatically stored to be used as data for next speckle energy analysis.

The storage unit 340 may be a read only memory (ROM), a programmable read only memory (PROM), an erasable programmable read only memory (EPROM), a non-volatile memory device such as a flash memory, a volatile memory device such as a random access memory (RAM), a hard disk, or an optical disk. However, the storage unit 340 is not limited to the above-mentioned devices, and may be implemented as any other storage device well-known in the art.

The display 160 may display an ultrasound image created by the image processing apparatus 350. More specifically, the display 160 may display a section image of an object or a 3D image of the object, created by the image processing apparatus 350, or may display the section image and the 3D image of the object at the same time.

At this time, the display 160 may display a location of an extracted target together. For example, if a target is included in an ultrasound image that is displayed, the display 160 may highlight an area of the target in the ultrasound image. More specifically, the display 160 may change the color or shadow of a target area, or the color or shadow of a boundary line of the target area. Alternatively, the display 160 may display a marker to inform a user of the location of a target area.

Now, a method in which the display 160 displays ultrasound images will be described in more detail, together with description about the controller 300.

According to an exemplary embodiment, the display 160 may display a final image restored after frequency decomposition and compounding.

The controller 300 may control image processing of ultrasound images, which is performed by the image processing apparatus 350, and control the display 160 to successively display a plurality of section images about an object created by the image processing apparatus 350.

More specifically, the controller 330 may control the display 160 to successively display a plurality of sections of an object located on a predetermined path at a predetermined frame rate.

Herein, the predetermined path may include a linear path, a curved path, or a circle path. The predetermined path may be determined by a user's input or by internal calculation of the ultrasound imaging apparatus.

Also, distances between the plurality of sections of the object and the predetermined frame rate may be determined by the user's input or by internal calculation of the ultrasound imaging apparatus.

If the controller 300 controls the display 160 to successively display a plurality of sections of an object, the display 160 can display a location of a target on the respective sections of the object.

A control flow of the speckle energy analyzer 351, the image decomposer 353, the image post processor 354, the image compounder 355, and the image restorer 356 included in the image processing apparatus 350 that is controlled by the controller 300 will be described in detail later.

Figure 3A:
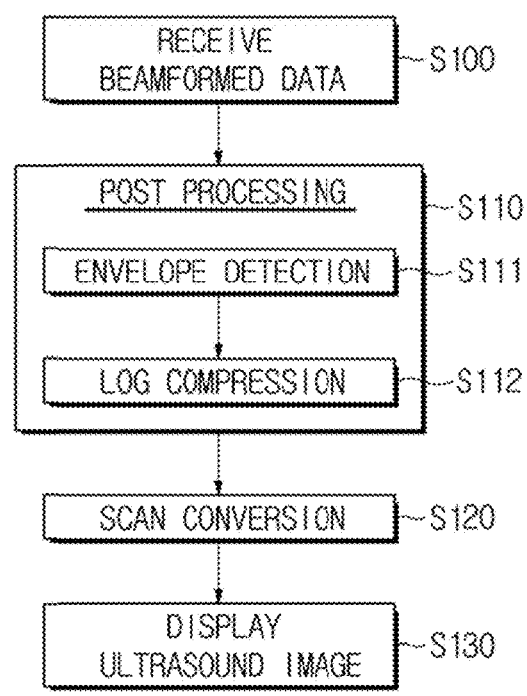
FIG. 3A is a flowchart illustrating an ultrasound image processing method according to an exemplary embodiment.

FIG. 3A is a flowchart illustrating an ultrasound image processing method according to an exemplary embodiment.

Referring to FIG. 3A, the image processing apparatus 350 may receive beamformed data, in operation S100, and perform post processing on the beamformed data, in operation S110. The post processing may include envelope detection (operation S111) and log compression (operation S112). In operation S111 of envelope detection, a broad-band radio frequency (RF) signal received and focused by the beamformer 200 may be divided into a plurality of signals of different frequency bands by a filter (not shown), the divided signals of the different frequency bands may be demodulated by a demodulation unit (not shown) and then envelopes may be detected from the demodulated signals by an envelope detector (not shown).

The envelope detector may detect envelopes of the signals according to the frequency bands. The signals from which envelopes have been detected according to the frequency bands may be added to form ultrasonic raw data, and then log compression and scan conversion may be performed on the ultrasonic raw data, thereby forming an ultrasound image.

A log compressor (not shown) may perform log compression on the signals from which envelopes have been detected by the envelope detector, in operation S112.

The reason of performing log compression is to convert signals into a dynamic range that can be recognized by a human's eyes to form images because probabilistic features of the magnitudes of demodulated signals have a Rayleigh distribution with a wide dynamic range. In other words, the reason of performing log compression is to adjust the brightness of ultrasound images by performing log compression on ultrasonic volume data using an image adjusting function (more specifically, a log function).

After envelope detection and log compression are performed, scan conversion may be performed in operation S120. The scan conversion is to convert ultrasound image information into video signals that can be displayed through the display 160, and then transmit the video signals to a volume rendering unit (not shown). That is, the scan conversion is to perform scan rate conversion on beamformed ultrasonic data so that the ultrasonic data can be displayed on a display area of the display 160. Thereafter, the display 160 may display the scan-converted ultrasonic data as an ultrasound image on the screen, in operation S130.

Since operation S110 of post processing and operation S120 of scan conversion are well known in the art, further detailed descriptions therefor will be omitted.

Figure 3B:
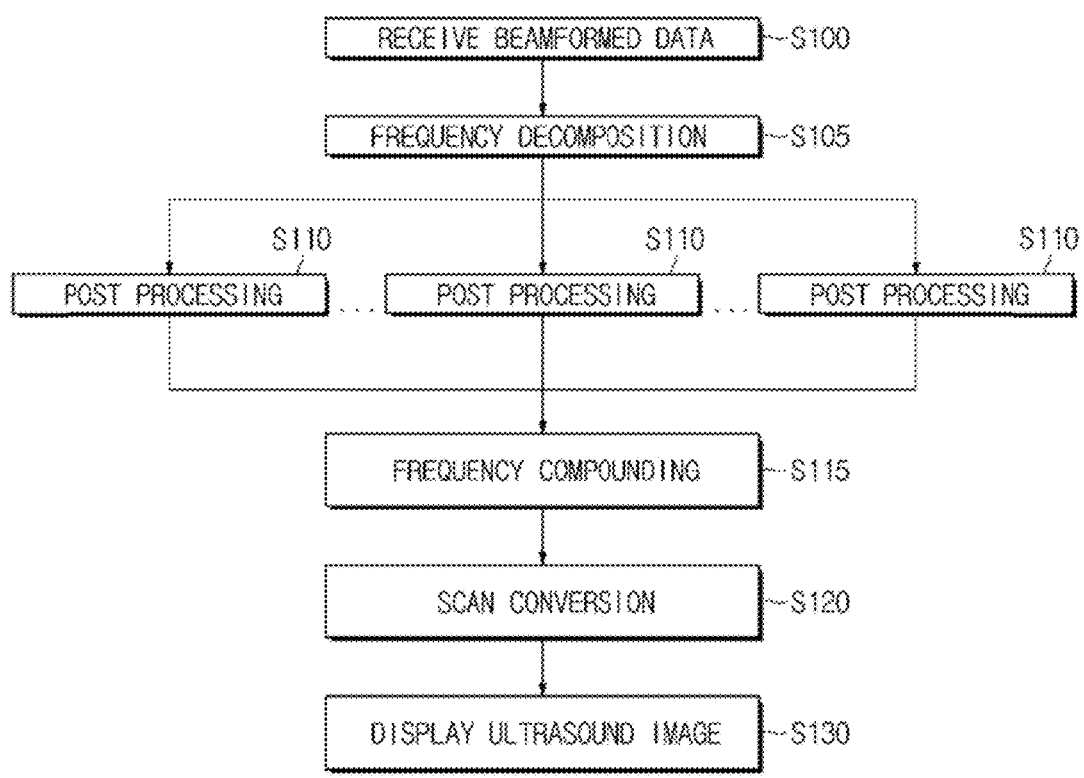
FIG. 3B is a flowchart illustrating an ultrasound image processing method including decomposition and compounding according to an exemplary embodiment.

FIG. 3B is a flowchart illustrating an ultrasound image processing method including decomposition and compounding according to an exemplary embodiment.

In the ultrasound image processing method of FIG. 3B, operation S110 of post processing and operation S120 of scan conversion are the same as those described above with reference to FIG. 3A.

However, in the ultrasound image processing method of FIG. 3B, operation S105 of decomposing beamformed ultrasound image signals may be further performed. Hereinafter, a method of decomposing ultrasound images will be described in detail with reference to FIGS. 3B to 5.

As shown in FIG. 2, the image processing apparatus 350 may include the image decomposer 353.

The image decomposer 353 may calculate an SNR of an ultrasound image corresponding to an input signal according to a frequency of the ultrasound image, and decompose the ultrasound image into one or more signals of different frequency bands, in operation S105. The ultrasound image may be decomposed based on the results of analysis on the ultrasound image. For example, the ultrasound image may be decomposed based on whether the ultrasound image includes harmonics components.

That is, the image decomposer 353 may decompose an ultrasound image corresponding to an input signal into one or more signals of different frequency bands.

An SNR of an ultrasound image in a frequency domain is high in a frequency area around fundamental or harmonic waves of the ultrasound image. The input signal is provided through ultrasound transmission/reception by the probe 110 and beamforming by the beamformer 200. If ultrasonic waves are transmitted to a target area, an intended effect is generated. The intended effect may be, for example, forming a 2D or 3D image of the target area, thermally deforming the target area, or destructing a part of cells in the target area, although not limited to these.

Ultrasonic waves (or incident waves) generated by the probe 110 may be distorted before or when arriving at an object, so that input signals corresponding to reflected waves include harmonic components.

While the incident waves arrive at a target area in the object, a part of the incident waves may be lost. However, according to an intended effect, about 60 to 80 percent of the incident waves is converted into heat at the target area, and the remaining about 20 to 40 percent of the incident waves is reflected as reflected waves. During conversion to heat, thermal deformation such as ambustion may occur, for example, in the subcutaneous tissue. If such thermal deformation occurs, small air bubbles may be generated, and the air bubbles may burst by ultrasonic waves. Due to such thermal deformation or bursting of small bubbles, the ultrasonic waves include a large amount of harmonic components. An amount of harmonic components that are included in the ultrasonic waves may depend on a degree of thermal deformation, an amount of generated bubbles, or a degree of bursting of bubbles. Generally, at the higher degree of thermal deformation, the greater amount of generated bubbles, or the higher degree of bursting of bubbles, the ultrasonic waves may include more harmonic components.

The "more harmonic components" means more physically meaningful harmonic components. For example, although harmonic waves of two, three, or four times (or more) of the frequency of fundamental waves can be generated (i.e., mathematically, harmonic waves corresponding to an arbitrary integer multiple of a fundamental frequency can be generated), harmonic components that can be received, decomposed, and compounded by the probe 110 may be harmonic components having magnitudes that are equal to or greater than a predetermined threshold value.

Harmonic components which will be described below means the "more harmonic components" as described above, and may be harmonic components that can be compounded as an ultrasound image after subject to physical separation, amplification, or noise removal.

Accordingly, the input signal may include fundamental components and harmonic components.

Hereinafter, an ultrasound image is assumed to include fundamental waves and second harmonic waves, however, the ultrasound image may include harmonic wave components, subharmonic wave components, or fractional wave components, having a frequency of an arbitrary integer multiple of fundamental waves.

Also, the "frequency area around fundamental or harmonic waves" may be a frequency area around fundamental or harmonic waves arbitrarily sampled by a controller, or may be a frequency area set by a user or a manufacturer. In the following description, the frequency area around fundamental or harmonic waves will be simply referred to as a frequency area.

Referring again to FIGS. 2 and 3A, the image decomposer 353 of the ultrasound imaging apparatus may increase a bandwidth of a second harmonic frequency area in inverse proportion to an SNR of the second harmonic frequency area. More specifically, the image decomposer 353 may set a band of a second harmonic frequency area by expanding the second harmonic frequency area to a fundamental frequency area such that an SNR of the second harmonic frequency area is equal to an SNR of the fundamental frequency area.

Figure 4A:
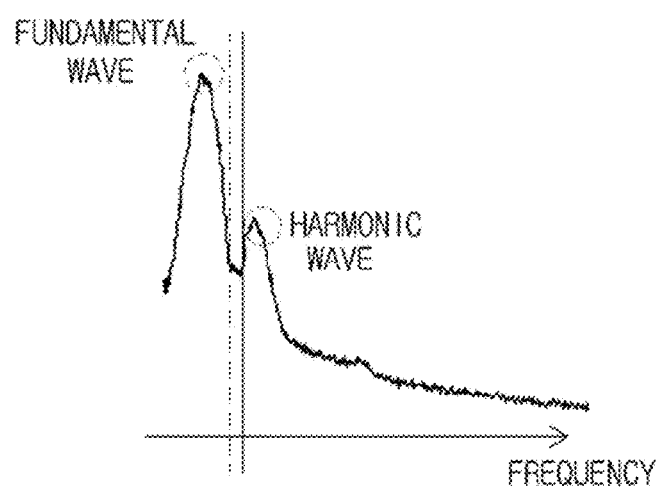
FIGS. 4A, 4B, and 4C are views for describing a method in which an image decomposer decomposes an ultrasound image according to an exemplary embodiment.
Figure 4B:
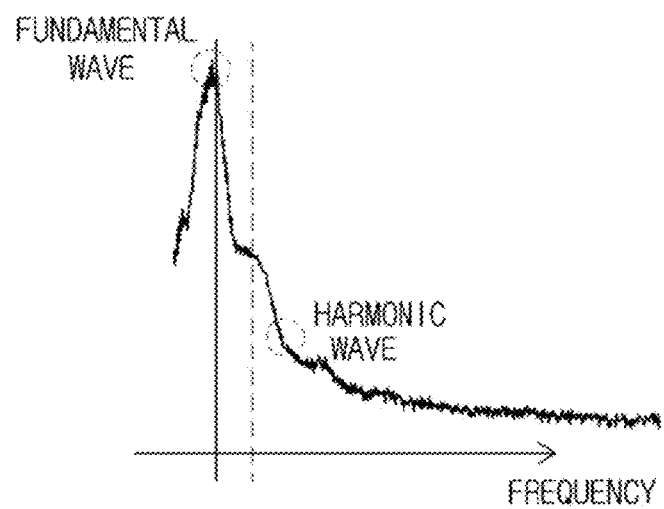
Figure 4C:
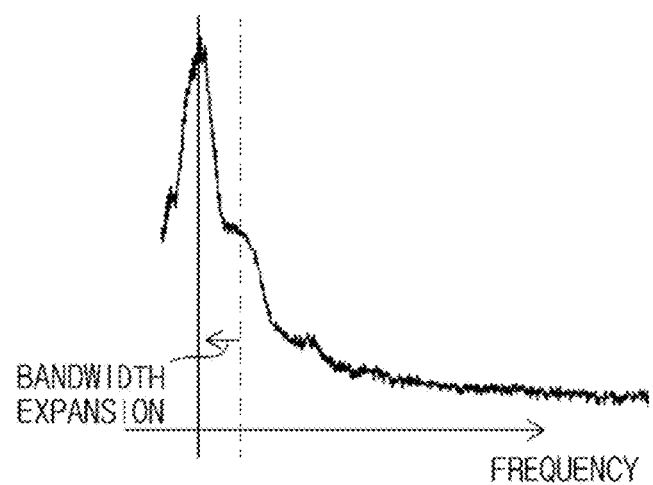

FIGS. 4A, 4B, and 4C are views for describing a method in which the image decomposer 353 decomposes an ultrasound image.

Referring to FIG. 4A, an SNR of a second harmonic frequency area of an ultrasound image has a great value so that the second harmonic frequency area can be clearly distinguished from a fundamental frequency area. Accordingly, the second harmonic frequency area of FIG. 4A may be allocated a relatively narrower bandwidth than a second harmonic frequency area of FIG. 4B.

Referring to FIG. 4B, an SNR of a second harmonic frequency area of an ultrasound image has a small value so that the second harmonic frequency area cannot be clearly distinguished from a fundamental frequency area. In this case, the image decomposer 353 may adjust a bandwidth such that the SNR of the second harmonic frequency area is equal to an SNR of the fundamental frequency area, to decompose the ultrasound image. That is, the second harmonic frequency area of FIG. 4B may be allocated a relatively wider bandwidth than the second harmonic frequency area of FIG. 4A.

More specifically, referring to FIG. 4C, the image decomposer 353 may expand the second harmonic frequency area of FIG. 4B to the fundamental frequency area to decompose the ultrasound image, in order to improve resolution of the ultrasound image.

Also, according to another exemplary embodiment, when an ultrasound image corresponds to a short distance area or a focused area, that is, when an ultrasound image is an image of a focused area or an area close to the focused area, the image decomposer 353 may expand a harmonic frequency area such that the bandwidth of the harmonic frequency area is wider than the bandwidth of the fundamental frequency area. Also, when an ultrasound image corresponds to a long distance area or a defocused area, the image decomposer 353 may reduce a harmonic frequency area such that the bandwidth of the harmonic frequency area is narrower than the bandwidth of the fundamental frequency area. Accordingly, the image decomposer 353 may remove speckle noise from an ultrasound image of a short distance area or a focused area without degrading resolution, and improve an SNR of an ultrasound image of a long distance area or a defocused area.

The image decomposer 353 may apply the same method to decompose a plurality of ultrasound images.

Figure 5:
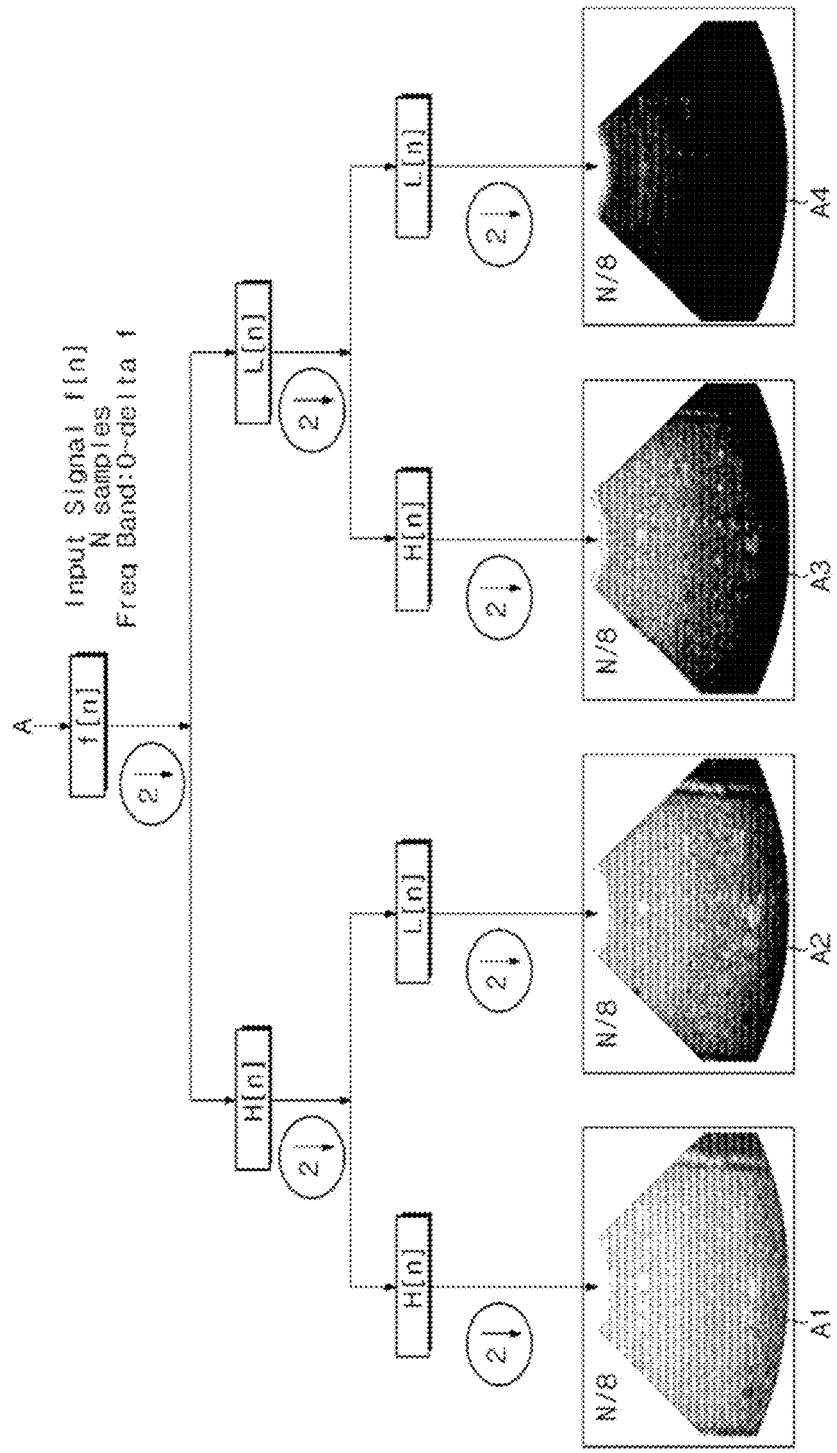
FIG. 5 is a view for describing frequency decomposition of an input image according to an exemplary embodiment.

FIG. 5 is a view for describing frequency decomposition of an input image.

FIG. 5 shows an example of frequency decomposition, wherein the number of areas into which an ultrasound image is decomposed may be more or less than that shown in FIG. 5. Also, the image decomposer 353 may decompose an ultrasound image based on different situational variables (for example, the velocity of sound or the depth of a target area).

As shown in FIG. 5, the image decomposer 353 may decompose an input image signal A according to frequency bands to create one or more images, under the control of the controller 350 (see FIG. 2).

In FIG. 5, "H" represents a high frequency, "L" represents a low frequency, and a figure "2" represents decomposing an image into two images. However, the number of images into which an ultrasound image is decomposed is not limited to two, and an ultrasound image can be decomposed into three images or more. As shown in FIG. 5, the input image signal A may be decomposed into a high-frequency image signal and a low-frequency image signal, and each of the high-frequency and low-frequency image signals may be again decomposed into a high-frequency image signal and a low-frequency image signal, thereby finally outputting four image signals A1, A2, A3, and A4. The image signals A1, A2, A3, and A4, which correspond to images decomposed from the input image signal A, may be output over frequency bands from a high frequency to a low frequency. As shown in FIG. 5, the image A1 is a clear image with the highest resolution, and the image A4 is a blur image with the lowest resolution. This indicates that the resolution of a decomposed image depends on a frequency area. That an ultrasound image signal includes a large amount of high-frequency components means that the ultrasound image signal has high speckle energy and high resolution (that is, excellent sharpness), and that an ultrasound image signal includes a large amount of low-frequency components means that the ultrasound image signal has low speckle energy and low resolution (that is, poor sharpness), which will be described later.

Referring again to FIGS. 2 and 3B, frequency compounding will be described.

The ultrasound imaging apparatus may compound the decomposed images in order to combine the decomposed images, in operation S115. More specifically, the image compounder 355 may compound the images of the different frequency bands by combining the images into an image and amplifying the intensity of a signal of a predetermined frequency band. The image compounder 355 may include an image combiner (not shown), a binary image creator (not shown), a contrast to noise ratio (CNR) calculator (not shown), and a weight applying unit (not shown).

The image combiner may combine restored images of different frequency bands to create a first combined image. The first combined image may be transmitted to the display 160 through a transceiver.

Based on comparison between the ultrasound image corresponding to the input signal and the first combined image created by the image combiner, it can be understood that the first combined image has high resolution and low noise compared to the ultrasound image.

According to another exemplary embodiment, the image processing apparatus 350 may compound the decomposed images adaptively using CNRs of the decomposed images to create a second combined image.

The image compounder 355 may include the image combiner to combine the decomposed images to create a combined image, and further include the binary image creator to binary-code a first combined image, the CNR calculator to calculate a CNR of an area of interest, and the weight applying unit to apply weights to the decomposed images.

The binary image creator may threshold the first combined image created by the image combiner based on a predetermined threshold value to divide a pixel area of the first combined image into a dark area or a bright area. The binary image creator may threshold the ultrasound image corresponding to the input signal based on the predetermined threshold value, other than the first combined image.

The predetermined threshold value may be set by a user. Also, the predetermined threshold value may be received through an input unit when the image processing apparatus 350 is used, or may have been set in advance when the image processing apparatus 350 is manufactured.

Next, the CNR calculator may calculate a CNR of an arbitrary area of interest of the bright area or the dark area. The CNR, which is a magnitude ratio of contrast to noise and also called contrast resolution, means relative signal intensity of the corresponding area to the background.

Then, the weight applying unit may apply a weight, calculated by a weight calculator of calculating a weight of a harmonic component for each area according to a CNR of the area, to the area.

For example, if the CNR calculator calculates a CNR of a first area of interest as 10 dB, and a CNR for a second area of interest as 20 dB, the weight applying unit may apply a greater weight to a decomposed image of a harmonic frequency band of the second area of interest, than to a decomposed image of a harmonic frequency band of the first area of interest.

That is, the weight applying unit may compare an average value of signal intensity of a decomposed image of a fundamental frequency band and signal intensity of a decomposed image of a harmonic frequency band, to a threshold value. If the average value is smaller than the threshold value, the weight applying unit may determine that the corresponding area is a dark area, and assign a weight for a harmonic component (for example, in a decomposed image for a second harmonic frequency band) of an area of interest according to a CNR, to the area. If the average value is greater than the threshold value, the weight applying unit may determine that the corresponding area is a bright area, and assign a predetermined weight to the area.

Also, a weight for a harmonic component (for example, in a restored image for a second harmonic frequency band) of an area of interest, which is assigned according to a CNR, may be a value that is proportional to the CNR.

Next, the image combiner may combine pixel areas to which weights for harmonic components (for example, in a decomposed image for a second harmonic frequency band) have been respectively assigned, to create a second combined image. The second combined image may be transferred to the display 160 through a transceiver.

Through image decomposition by the image decomposer 353 and image compounding by the image compounder 355, a CNR of a dark area can be improved so that a combined image with reduced cluster noise can be created.

Operation S105 of frequency decomposition and operation S115 of frequency compounding have been described above with reference to FIG. 3B, and descriptions about the remaining operations except for operations S105 and S115 have been described above with reference to FIG. 3A. Therefore, further repetitive descriptions therefor will be omitted.

Figure 6:
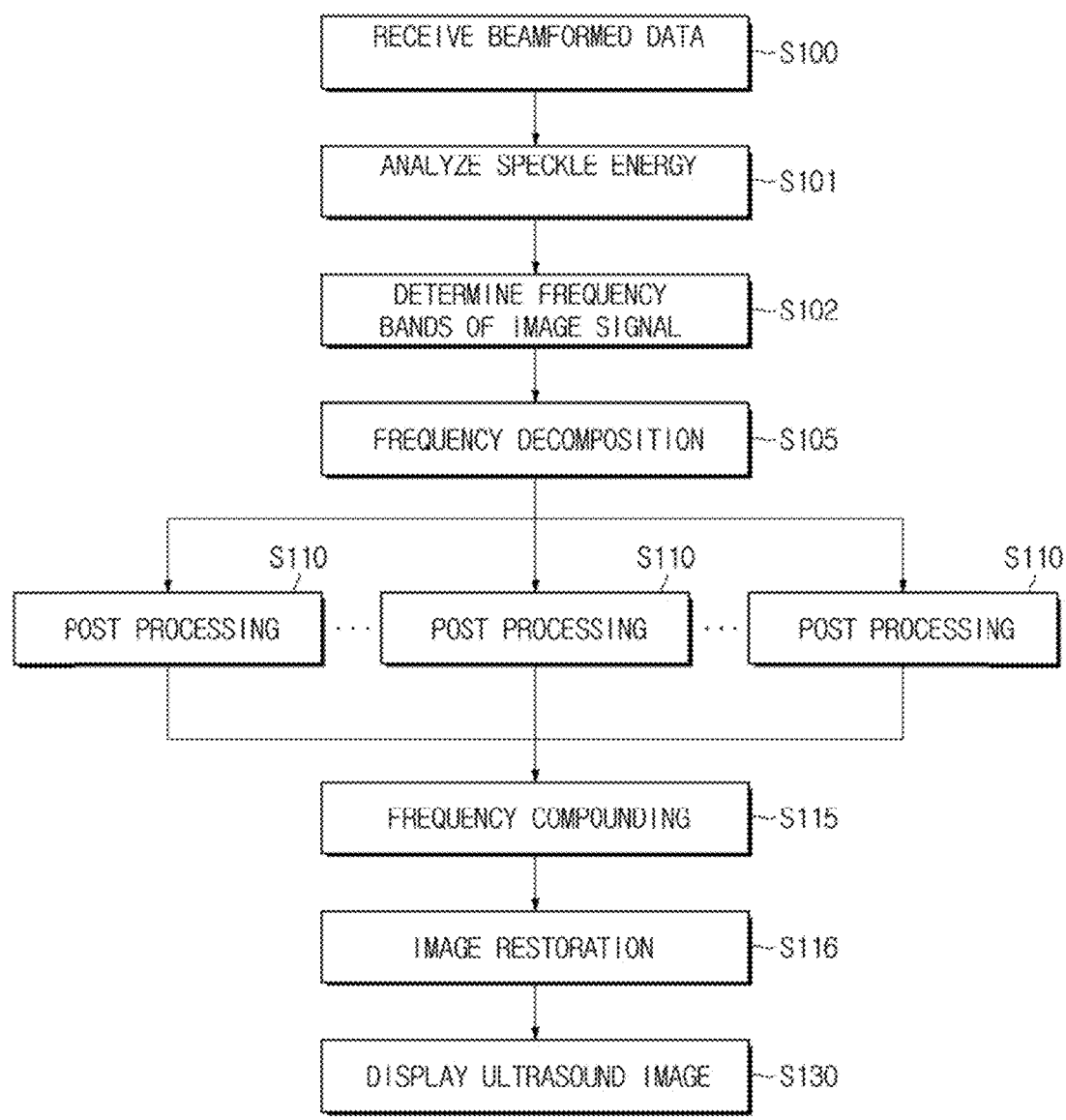
FIG. 6 is a flowchart illustrating a control method of an image processing apparatus according to an exemplary embodiment.

FIG. 6 is a flowchart illustrating a control method of an image processing apparatus that analyzes speckle energy of an ultrasound image signal according to a depth of the ultrasound image signal, decomposes the ultrasound image signal according to frequency bands, and then compounds the decomposed image signals to restore an image, according to an exemplary embodiment.

Hereinafter, an exemplary embodiment will be described in detail with reference to FIGS. 2 and 5 to 9.

Referring to FIG. 6, beamformed data may be received, in operation S100, and speckle energy of an ultrasound image signal may be analyzed according to depths of the ultrasound image signal, in operation S101. The speckle energy of the ultrasound image signal may be analyzed by the speckle energy analyzer 351 of the image processing apparatus 350. Herein, the speckle is a small speckle appearing in the ultrasound image, and corresponds to ultrasonic noise. The speckle energy of the ultrasound image signal represents a difference between a pixel value of a small speckle included in the ultrasound image and a pixel value of an area adjacent to the speckle. If a difference between a pixel value of a pixel corresponding to a speckle and a pixel value of an area adjacent to the speckle is great, high speckle energy is determined, and if the difference between the pixel values is small, low speckle energy is determined. In order to determine the magnitude of speckle energy, a speckle energy value of an image signal that is to be analyzed may be compared to a predetermined speckle energy value. Herein, the predetermined speckle energy value, which is data stored in advance in the storage unit 340, may have been input by a user's input, or may have been stored as a resultant value calculated through speckle energy analysis of image signals.

High speckle energy indicates that the corresponding image signal has high resolution (excellent sharpness) and includes a large amount of high-frequency components, and low speckle energy indicates that the corresponding image signal has low resolution, appears as a blur image, and includes a relatively large amount of low-frequency components and a relatively small amount of high-frequency components.

The reason of analyzing speckle energy is to reduce speckle noise and improve resolution according to decomposed images by determining optimal frequency bands for decomposition based on the analyzed speckle energy and compounding images decomposed according to the optimal frequency bands, because images decomposed from a beamformed ultrasound image signal according to multiple frequency bands have different speckle patterns and different speckle energy levels due to the different frequency areas.

The speckle energy analyzer 351 may analyze speckle energy of input image signals in the depth direction of the input image signals.

The reason of analyzing speckle energy of input image signals in the depth direction of the input image signals is to determine frequency bands of the image signals according to the depths of the images through analysis of speckle energy based on depth, and to apply the determined frequency bands to decomposition, since ultrasound image signals generated by examining an object using the ultrasound probe 110 appear more blur at a deeper region, that is, at a region of the object that is more distant from the ultrasound probe 110. Since echo ultrasonic signals reflected from the deeper region of an object have lower intensity, the ultrasound image signals appear more blur and have low speckle energy at the deeper region.

Figure 7A:
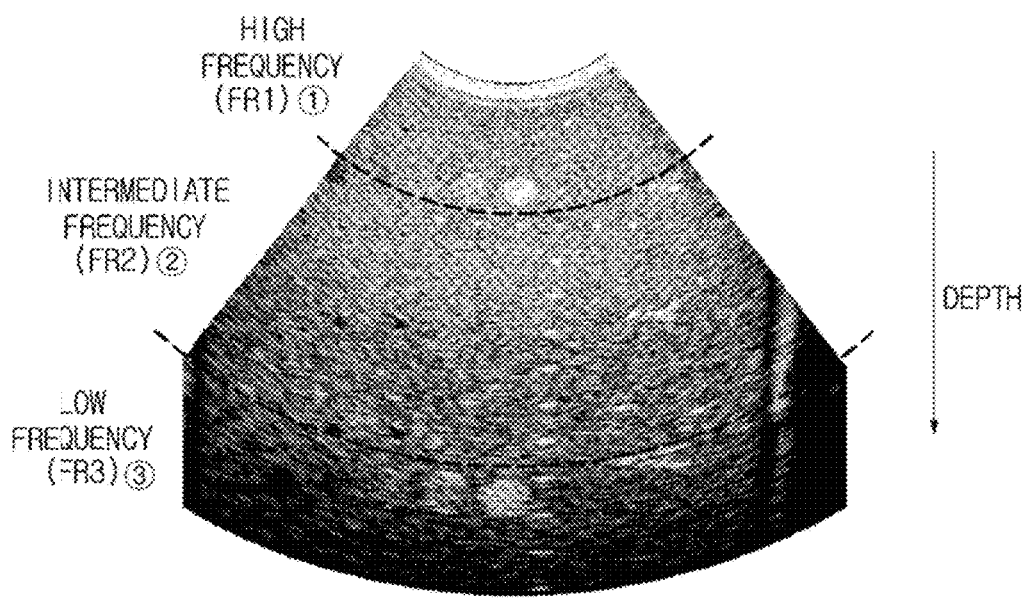
FIGS. 7A and 7B are views for describing units in which speckle energy of an ultrasound image signal is analyzed, according to an exemplary embodiment.
Figure 7B:
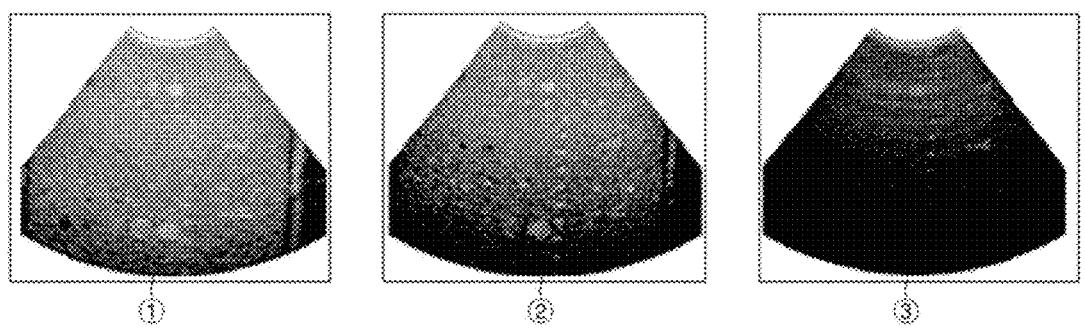

FIGS. 7A and 7B are views for describing units in which speckle energy of an ultrasound image signal is analyzed, according to an exemplary embodiment.

As shown in FIG. 7, speckle energy of an ultrasound image signal may be analyzed in units of depths of the image (see FIG. 7A), or in units of decomposed ultrasound images (see FIG. 7B).

Referring to FIG. 7A, an input image may be divided into three images ①, ②, and ③ according to predetermined depths. Referring to FIG. 7B, the images ①, ②, and ③ may correspond to the deeper depths in this order. That is, an ultrasound image signal of the image ③ may be received with lower intensity than an ultrasound image signal of the image ①. The images ①, ②, and ③ may be divided into a high-frequency area FR1, an intermediate-frequency area FR2, and a high-frequency area FR3. The signal of the image ③ may correspond to a relatively lower-frequency area than the signal of the image ①, and has low speckle energy, so that the image ③ has relatively low resolution and appears to be more blur. The signal of the image ① has higher speckle energy, higher resolution, and more speckle noise than the signal of the image ③.

Also, referring to FIG. 7B, the image ① to the image ③, on which frequency decomposition has been performed, have low resolution and appear to be blur in this order. As shown in FIG. 7B, images decomposed from an ultrasound input image have different speckle energy levels, different resolution, and different frequency components. Also, as shown in FIG. 7B, the signal of the image ① have higher speckle energy, higher resolution, and more speckle noise than the signal of the image ③.

Referring again to FIG. 6, after the speckle energy analyzer 351 analyzes speckle energy of the ultrasound image according to depths of the ultrasound image, the image processing apparatus 350 may determine one or more frequency bands of an image signal that is to be decomposed, based on the analyzed speckle energy data, in operation S102. Determining one or more frequency bands of an image signal is to move an image signal having high speckle energy to a low-frequency band and move an image signal having low speckle energy to a high-frequency band, based on the magnitudes of speckle energy at different depths of the image signal, thereby decomposing the image. Moving a frequency band may be moving a frequency band for each depth to a desired frequency band, or decomposing an image by applying a predetermined frequency band value to the image.

As described above, that an image signal has high speckle energy means that the image signal has high resolution (excellent sharpness) and a large amount of high-frequency components, as seen from the image ① at a shallow depth of FIGS. 7A and 7B. Accordingly, when a frequency band of an image signal having high speckle energy is determined, the image signal is adjusted to a low-frequency band in order to reduce speckle noise, instead of adjustment to a high-frequency band or improvement of resolution, and the adjusted frequency band is reflected to decomposition.

Also, that an image signal has low speckle energy means that the image signal has low resolution, appears to be blur, and has a relatively large amount of low-frequency components and a relatively small amount of high-frequency components, as seen from the image ③ at a deep depth of FIGS. 7A and 7B. Accordingly, if a frequency band of an image signal having low speckle energy is determined, the image signal is adjusted to a high-frequency band in order to improve resolution, instead of reduction of speckle noise, and the adjusted frequency band is reflected to decomposition.

Figure 9:
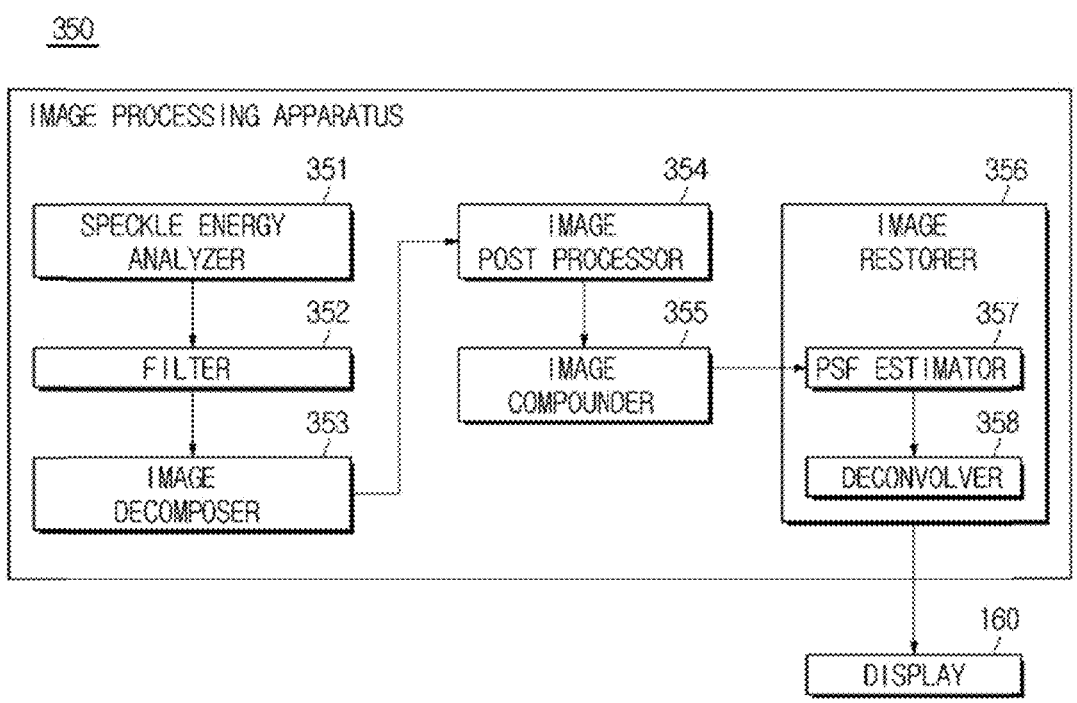
FIG. 9 is a control block diagram of an image processing apparatus according to an exemplary embodiment.

As shown in FIGS. 2 and 9, if one or more frequency bands of an image are determined and frequency decomposition is performed, the filter 352 of the image processing apparatus 350 may perform filtering to determine one or more frequency bands of an image signal, and the image decomposer 353 may decompose the image signal into one or more signals of different frequency bands based on the determined frequency bands.

This operation will be described in detail with reference to FIGS. 2, 8, and 9, below.

Figure 8A:
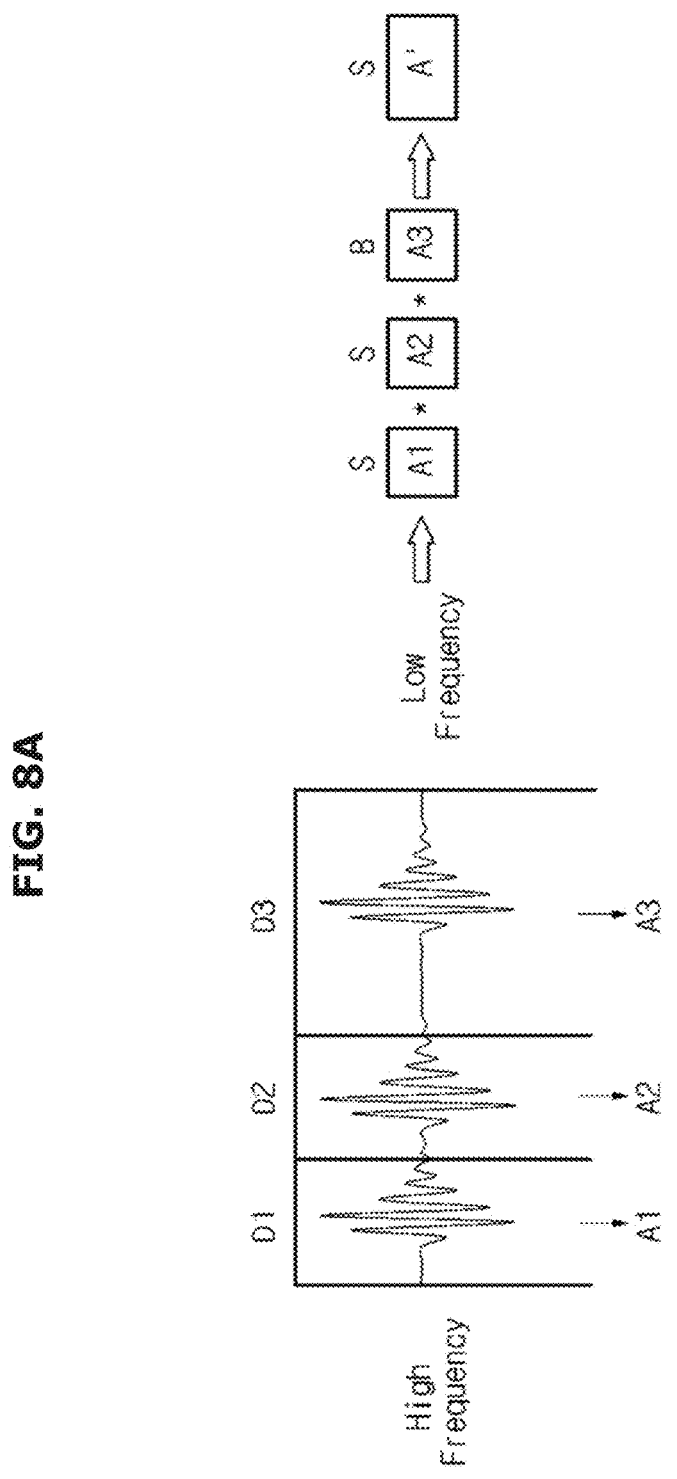
FIGS. 8A and 8B are views for describing a filtering process for decomposing an image according to determined frequency bands, according to an exemplary embodiment.
Figure 8B:
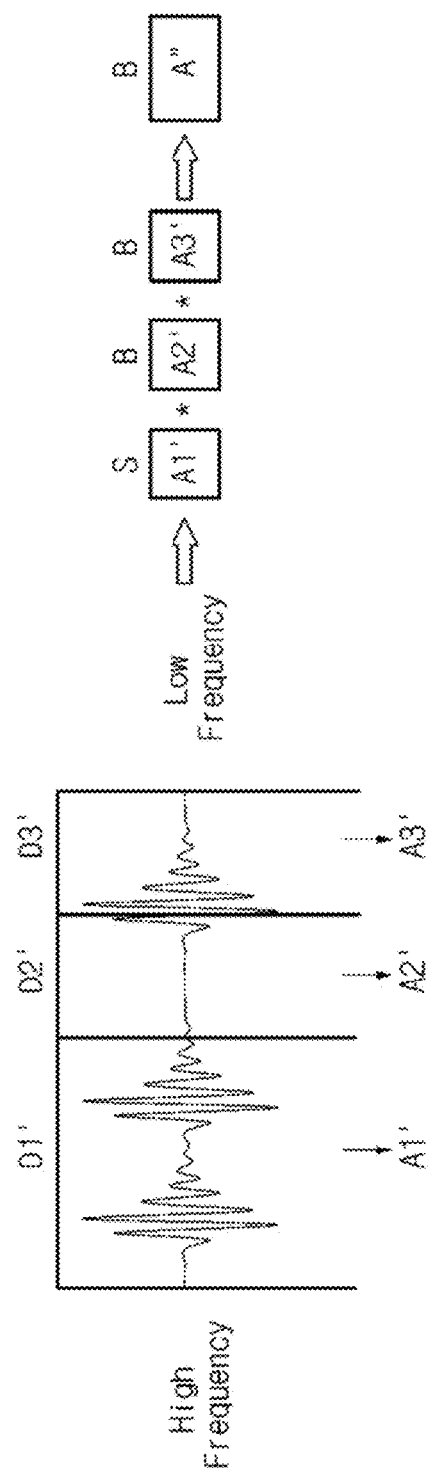

FIGS. 8A and 8B are views for describing a filtering process for decomposing an image according to determined frequency bands, according to an exemplary embodiment.

FIG. 8A is a view for describing a filtering process for outputting a high-frequency band, that is, an image signal with high resolution (excellent sharpness), and FIG. 8B is a view for describing a filtering process for outputting a low-frequency band, that is, an image signal with reduced speckle noise.

In FIG. 8A, D1, D2, and D3 represent the filter 352 that performs filtering to select image signals according to frequency bands. The D1, D2, and D3 may be dynamic filters. Also, A1, A2, and A3 are three images decomposed from an input image A. In FIG. 8B, D1', D2', and D3' represent the filter 352, and A1, A2, and A3 represent decomposed images. However, the number of decomposed images is not limited to three, and the number of dynamic filters corresponding to the filter 352 may vary depending on the number of images by which an image is to be decomposed. Also, a waveform that is filtered by the filters is a waveform of an input image signal, wherein the left part of the waveform is a high-frequency band and the right part of the waveform is a low-frequency band. The filters may be applied according to the frequency bands. Also, "S" represents "Sharp" and means an image signal with high resolution, that is, a high-frequency band signal, and B represents "Blur" and means an image signal with low resolution that will appear as a blur image, that is, a low-frequency band signal.

In the filtering process as shown in FIG. 8A, when an input image signal is analyzed to have low speckle energy so that the input image signal has to be decomposed into a high-frequency band in order to improve resolution, the filters D1 and D2 are positioned in the high-frequency band of the image signal, and the filter D3 is positioned in the low-frequency band so that the respective filters D1, D2, and D3 output image signals of the corresponding frequency bands. Whether an image signal corresponds to a high-frequency band or a low-frequency band is relatively determined, and a band or range of an image signal is selected according to the analyzed speckle energy of the image signal. The filtering process shown in FIGS. 8A and 8B is only exemplary.

In FIG. 8A, if an image of a frequency band selected from the filter D1 is referred to as A1, an image of a frequency band selected from the filter D2 is referred to as A2, and an image of a frequency band selected from the filter D3 is referred to as A3, the images A1 and A2 correspond to image signals with high resolution (excellent sharpness) since the images A1 and A2 are based on image signals of a high-frequency band, and the image A3 corresponds to an image signal with low resolution (appearing as a blur image) since the image A3 is based on an image signal of a low-frequency band. Accordingly, an output image A' obtained by compounding the images A1, A2, and A3 is more influenced by the image signals of the high-frequency band, so that the output image A' has high resolution and includes a large amount of high-frequency components. In summary, by determining image signals as predetermined frequency bands based on the results of analysis on the speckle energy of the image signals, decomposing the image signals according to the determined frequency bands, and then compounding the decomposed image signals, the resultant image A' that is moved to a high-frequency band with respect to the input image A can be output.

In the filtering process as shown in FIGS. 8A and 8B, frequency decomposition and frequency compounding have been described above with reference to FIGS. 2, 3A, and 3B (see operations S105 and S115), and accordingly, further repetitive descriptions therefor will be omitted.

In the filtering process as shown in FIG. 8B, when an input image signal is analyzed to have high speckle energy and include a large amount of high-frequency components so that the input image signal has to be decomposed into a low-frequency band in order to reduce speckle noise, instead of improving resolution, the filter D1' is positioned in the high-frequency band of the image signal, and the filters D2' and D3' are positioned in the low-frequency band so that the respective filters D1', D2', and D3' output image signals of the corresponding frequency bands.

In FIG. 8B, if an image of a frequency band selected from the filter D1' is referred to as A1', an image of a frequency band selected from the filter D2' is referred to as A2', and an image of a frequency band selected from the filter D3' is referred to as A3', the image A1' corresponds to an image signal with high resolution (excellent sharpness) since the image A1' is based on an image signal of a high-frequency band, and the images A2' and A3' correspond to image signals with low resolution (appearing as blur images) since the images A2' and A3' are based on image signals of a low-frequency band. Accordingly, an output image A" obtained by compounding the images A1', A2', and A3' is more influenced by the image signals of the low-frequency band, so that the output image A" is output as an image signal having reduced speckle noise and including a large amount of low-frequency components. In summary, by determining image signals as predetermined frequency bands based on the results of analysis on the speckle energy of the image signals, decomposing the image signals according to the determined frequency bands, and then compounding the decomposed image signals, the resultant image A" that is moved to a low-frequency band with respect to the input image A can be output.

That is, the filter 352 may determine one or more frequency bands for an input image signal, and select image signals of the determined frequency bands before decomposition.

Operation of selecting image signals according to frequency bands may be performed by determining frequency bands according to the depths of ultrasound image signals before decomposition or by selecting frequency bands determined based on the analyzed speckle energy of images after decomposition and before compounding. Operation of analyzing the speckle energy of images and selecting frequency bands after decomposition and before compounding will be described later.

As shown in FIG. 7A, different speckle energy levels and different frequency bands appear according to the depths of ultrasound image signals, and as shown in FIG. 7B, different speckle energy levels and different frequency bands appear in units of images after decomposition.

FIG. 7A shows that input ultrasound image signals have different speckle energy levels according to depths, and as shown in FIG. 7A, the filter 352 may determine frequency bands of an image according to depths, based on speckle energy values based on depths. Accordingly, frequency bands of an ultrasound image signal or a decomposed image may be determined according to depths. However, a method of determining frequency bands of an ultrasound image signal is not limited to this.

Referring again to FIG. 6, frequency decomposition may be performed according to the determined frequency bands of the image signal, as described above with reference to FIGS. 8A and 8B, in operation S105. The number of images into which the image signal is decomposed is not limited. That is, the number of images into which an image signal is decomposed, as described in the specification, is only exemplary. After frequency decomposition is performed, the image post processor 354 may perform post processing on each of the decomposed images, in operation S110. The post processing has been described above with reference to FIG. 3A, and accordingly, further repetitive descriptions therefor will be omitted.

The image compounder 355 may perform frequency compounding on the images subject to post processing to create a compounded image, in operation S115. The frequency compounding has been described above with reference to FIGS. 2 and 3B, and accordingly, further repetitive descriptions therefor will be omitted.

Then, the image restorer 356 may perform restoration on the compounded image in operation S116. The restoration will be described in detail with reference to FIGS. 2 and 9 to 11, later.

The reason of performing restoration is to prevent axial resolution degradation that may occur during frequency compounding. Since compounding is to compound images of narrow frequency bands, a side-lobe, in which a main ultrasound image signal spreads axially, occurs, resulting in resolution degradation. Accordingly, 1D parametric cepstrum point spread function (PSF) estimation and restoration are used after compounding in order to restore the resolution of the ultrasound image signal. In a conventional method, estimation and restoration have been performed on individual decomposed images before compounding, however, the conventional method results in an increase of complexity since restoration is performed on each image. However, according to an exemplary embodiment, estimation and restoration are performed on a compounded image, and thus, axial resolution can be improved with low complexity.

The image processing apparatus 350 may include the transceiver (not shown), the image restorer 356, the image post processor 354, and the image compounder 355.

The image processing apparatus 350 may estimate a PSF of an ultrasound image, and perform deconvolution based on the estimated PSF to acquire a restored image that is similar to an original image of a target area.

The original image and the restored image will be described in more detail with reference to FIGS. 10A, 10B, and 11, below.

Figure 10A:
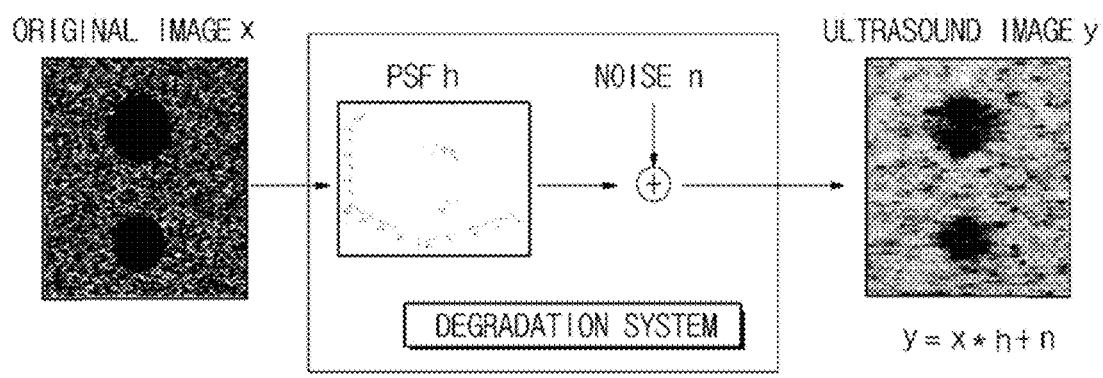
FIG. 10A is a view for describing a relationship between an original image and an ultrasound image with respect to a target area of an object according to an exemplary embodiment.
Figure 10B:
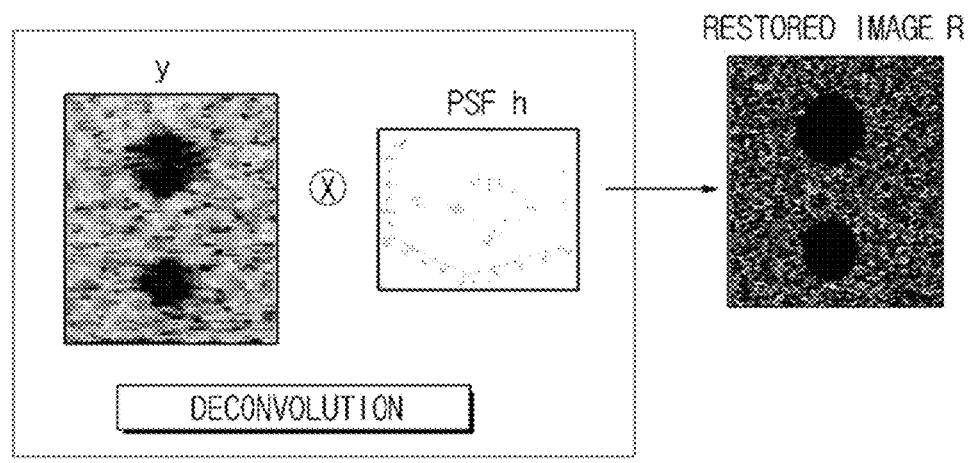
FIG. 10B is a view for describing a relationship between an ultrasound image and a restored image with respect to the target area of the object according to an exemplary embodiment.

FIG. 10A is a view for describing a relationship between an original image and an ultrasound image with respect to a target area of an object, and FIG. 10B is a view for describing a relationship between the ultrasound image and a restored image with respect to the target area of the object.

In FIG. 10A, an original image x and an ultrasound image y are shown. In FIG. 10B, the ultrasound image y and a restored image R are shown. The original image x is an ideal image that is desired to be acquired for a target area of an object, and the ultrasound image y is an image created according to an input signal. Also, the restored image R is an image restored from the ultrasound image y such that the restored image is similar to the original image x.

As described above, the input signal is provided through ultrasound transmission/reception by the probe 110 and beamforming by the beamformer 200. If ultrasonic waves are transmitted to a target area, an intended effect is generated. The intended effect may be, for example, forming a 2D or 3D image of the target area, thermally deforming the target area, or destructing a part of cells in the target area, although not limited to these.

Ultrasonic waves (or incident waves) generated by the probe 110 may be distorted before or when arriving at an object, so that input signals corresponding to reflected waves include harmonic components.

While incident waves arrive at a target area in a human body, the incident waves may be distorted so that an intended effect such as thermal deformation is generated at the target area, and then the waves may be received as reflected waves by the probe 110.

While the incident waves arrive at a target area in the object, a part of the incident waves may be lost. However, according to the intended effect, about 60 to 80 percent of the incident waves may be converted into heat at the target area, and the remaining about 20 to 40 percent of the incident waves may be reflected as reflected waves. During conversion to heat, thermal deformation such as ambustion may be made, for example, in the subcutaneous tissue. If such thermal deformation is made, small air bubbles may be generated, and the air bubbles may burst by ultrasonic waves. Due to such thermal deformation or burst of small bubbles, the ultrasonic waves may include a large amount of harmonic components. An amount of harmonic components that are included in the ultrasonic waves may vary depending on a degree of thermal deformation, an amount of generated bubbles, or a degree of bursting of bubbles. Generally, at the higher degree of thermal deformation, the greater amount of generated bubbles, or the higher degree of bursting of bubbles, the ultrasonic waves may include more harmonic components.

The "more harmonic components" means physically meaningful harmonic components. For example, although harmonic waves of two, three, or four times (or more) of the frequency of fundamental waves can be generated (i.e., mathematically, harmonic waves corresponding to an arbitrary integer multiple of a fundamental frequency can be generated), harmonic components that can be received, decomposed, and compounded by the probe 110 may be harmonic components having magnitudes that are equal to or greater than a predetermined threshold value.

Harmonic components which will be described below means the "more harmonic components" described above, and may be harmonic components that can be compounded as an ultrasound image after subject to physical separation, amplification, or noise removal.

Accordingly, the input signal may include the fundamental components and harmonic components.

Also, the input signal have been distorted due to the technical properties or physical characteristics of the probe 110 or the beamformer 200, and include noise n. Accordingly, the ultrasound image y created according to the input signal is blur, includes noise, and has degraded picture quality compared to the original image x, as shown in FIG. 10A. A relationship between the original image x and the ultrasound image y with respect to the noise n will be described in more detail with reference to FIGS. 11A and 11B, below.

Figure 11A:
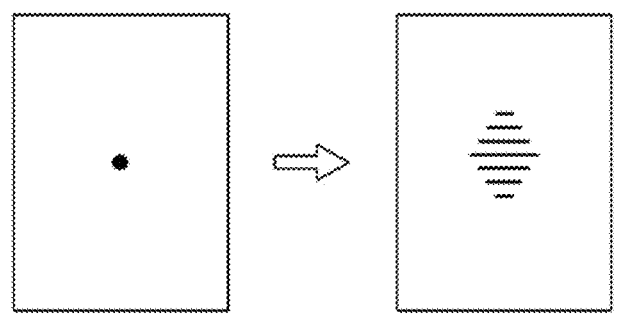
FIGS. 11A and 11B are views showing original images and ultrasound images with respect to a target area according to an exemplary embodiment.
Figure 11B:
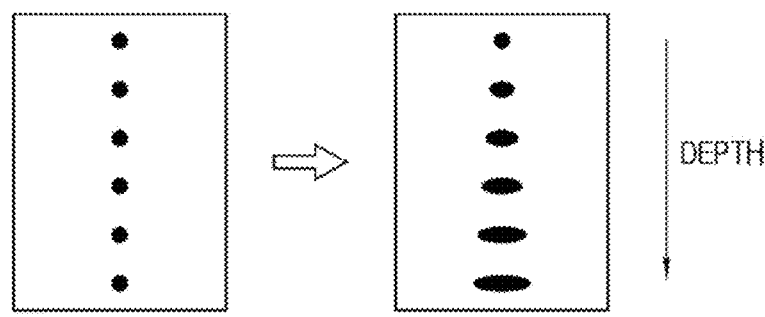

FIGS. 11A and 11B are views showing original images and ultrasound images with respect to a target area.

In FIG. 11A, an original image and an ultrasound image with respect to a target area are shown on the left and right. As shown in FIG. 11A, a target area, which is displayed as a dot in an original image, may be displayed as a shape spreading in up, down, left, and right directions in an ultrasound image. The difference between the original image and the ultrasound image appears more significant at the deeper depth of the target area. Herein, the deeper depth of the target area can be defined as the greater axial coordinates.

In FIG. 11B, an original image and an ultrasound image for a plurality of target areas at different depths are shown on the left and right. As shown in FIG. 11B, the target area of the ultrasound image, located close to the probe 110, is similar to the target area of the original image, whereas the target area of the ultrasound image, located distant from the probe 110, is greatly different from the target area of the ultrasound image.

As described above, due to the technical properties or physical characteristics of the probe 110 or the beamformer 200 and the noise n, the ultrasound image y with degraded picture quality is created. If deformation due to the technical properties or physical characteristics of the probe 110 or the beamformer 200 is expressed as a PSF h and the noise is represented by n, the relationship between the original image x and the ultrasound image y in the spatial domain can be expressed as Equation (1), below.

$$y = x*h + n, \quad (1)$$

where x represents the original image, y represents the ultrasound image, h represents the PSF, n represents the noise, and * represents convolution.

If no noise exists, the ultrasound image y can be expressed by convolution of the original image x and the PSF h. Accordingly, if the PSF h is obtained, the original image x corresponding to the ultrasound image y can be acquired by deconvolving the ultrasound image y with the PSF h.

Therefore, as shown in FIG. 10B, the image processing apparatus 350 may acquire a restored image R that is similar to the original image x of the target area by estimating an appropriate PSF h, and deconvolving the estimated PSF h with the ultrasound image y.

In order to acquire a restored image R that is more similar to the original image x, the image processing apparatus 350 may decompose an ultrasound image corresponding to an input signal so as to check meaningful harmonic components, such as thermal deformation or bursts of small bubbles of an object, deconvolve each composed ultrasound image y with an estimated PSF h, and then compound the results of the deconvolution as an ultrasound image.

More specifically, a transceiver connected to the beamformer 200 or the display 160 through a network may receive an image from the beamformer 200, and the image restorer 356 may estimate a PSF based on an ultrasound image compounded after frequency decomposition. Then, the image restorer 356 may perform deconvolution using the estimated PSF to acquire a restored image for the ultrasound image. Then, the image restorer 356 may again estimate a PSF to perform deconvolution. By repeatedly performing the process described above, an appropriate PSF can be estimated, and a finally acquired, restored image may be the same as or similar to an original image of a target area.

Configurations of the image compounder 355, the image post processor 354, and the image restorer 356 and a relationship between the configurations will be described in more detail with reference to FIG. 9, below.

FIG. 9 is a control block diagram of an image processing apparatus according to an exemplary embodiment.

Referring to FIG. 9, the image restorer 356 may include a PSF estimator 357 and a deconvolver 358.

The ultrasound imaging apparatus may perform deconvolution on an ultrasound image subject to frequency compounding. For deconvolution, the PSF estimator 357 may estimate at least one PSF for the ultrasound image. The estimated PSF may include a 1D PSF, a 2D PSF, or both a 1D PSF and a 2D PSF. According to an exemplary embodiment, the estimated PSF may include a 3D PSF, a four dimensional (4D) PSF, or a higher dimensional PSF.

An example of a method of estimating a 1D PSF may be Autoeyessive Moving Average (ARMA). The ARMA enables quick estimation of a PSF.

An example of a method of estimating a 2D PSF may be Cepstrum. The Cepstrum is a method of transforming an ultrasound image in the spatial domain into a Cepstrum domain, and then estimating a 2D PSF in the Cepstrum domain.

The Cepstrum is classified into a method of estimating a 2D PSF in consideration of only the magnitude information of an ultrasound image, and a method of estimating a 2D PSF in consideration of both the magnitude information and phase information of an ultrasound image. The method of estimating a 2D PSF in consideration of only the magnitude information of an ultrasound image enables quick estimation, and the method of estimating a 2D PSF in consideration of both the magnitude information and phase information of an ultrasound image enables accurate estimation.

In an exemplary embodiment, in order to prevent axial resolution degradation that may occur during frequency compounding, 1D Cepstrum PSF estimation and restoration are performed axially so as to improve axial resolution with low complexity, instead of performing restoration laterally.

The convolution unit 358 may deconvolve the PSF estimated by the PSF estimator 357 with the ultrasound image compounded after frequency decomposition, to create a restored image for the ultrasound image. According to an exemplary embodiment, the image restorer 356 may perform deconvolution using the deconvolver 358. However, the image restorer 356 may include a demodulation unit (not shown) to demodulate modulated ultrasound images.

The deconvolution may be performed using Equation (2), below.

$$R = DFT^{-1}\left[\frac{DFT(y)}{DFT(h)}\right] \quad (2)$$

where R represents the restored image, y represents the compounded ultrasound image, and h represents a PSF.

The deconvolver 358 may deconvolve the ultrasound image y with the PSF h using Equation (2) to create the restored image R.

More specifically, if a PSF h1 is estimated in correspondence to an ultrasound image of a fundamental frequency band, the deconvolver 358 may deconvolve the ultrasound image of the fundamental frequency band with the PSF h1 to create a first restored image R1.

Also, if a PSF h2 is estimated in correspondence to an ultrasound image of a harmonic frequency band, the deconvolver 358 may deconvolve the ultrasound image of the harmonic frequency band with the PSF h2 to create a second restored image R2.

Also, the ultrasound imaging apparatus may perform filtering on the restored image. The filtering is different from filtering for selecting frequency bands of an image signal according to an exemplary embodiment. Since the filtering is well known in the art, a detailed description therefor will be omitted.

A process of restoring an image subject to frequency compounding using 1D Cepstrum PSF estimation and restoration has been described above. The restored image may be displayed through the display 160. The images that are displayed through the display 160 may have reduced speckle noise, have improved contrast and resolution, or have improved axial resolution, according to the frequency bands.

Also, according to an exemplary embodiment, instead of analyzing speckle energy of ultrasound images according to depths, speckle energy may be analyzed in units of decomposed ultrasound images. More specifically, if beamformed data is received and frequency decomposition is performed on the beamformed data, a plurality of decomposed image signals may be output. At this time, the speckle energy analyzer 351 may analyze the speckle energy of the individual decomposed images in units of images. As described above with reference to FIG. 7B, the image ① corresponds to a high-frequency area having high speckle energy, and the image ③ corresponds to a low-frequency area having low speckle energy. Accordingly, based on speckle energy analyzed in units of images, the image ① is determined as a low-frequency band and then filtered in order to reduce speckle noise, and the image ③ is determined as a high-frequency band and then filtered in order to improve resolution. In other words, frequency compounding is performed on image signals filtered according to frequency bands determined based on speckle energy analyzed with respect to the individual decomposed images. As a result, it is possible to reduce the speckle noise of image signals with high speckle energy among the decomposed image signals, and to improve the resolution of image signals with low speckle energy among the decomposed image signals.

Accordingly, frequency band adjustment may be performed when the speckle energy of an ultrasound image signal is analyzed before frequency decomposition and then decomposition is performed, and when the speckle energy of decomposed images is analyzed after frequency decomposition and then the images are compounded.

The ultrasound imaging apparatus for analyzing the speckle energy of an ultrasound image signal, performing frequency decomposition based on the analyzed speckle energy, and then performing frequency compounding to restore an image, thereby improving axial resolution, the control method of the ultrasound imaging apparatus, and the ultrasound imaging apparatus have been described above with reference to the appended drawings.

However, the image processing apparatus, the control method of the image processing apparatus, and the ultrasound imaging apparatus are not limited to the exemplary embodiments described above.

According to the image processing apparatus, the control method of the image processing apparatus, and the ultrasound imaging apparatus, it is possible to uniformly reduce speckle noise and improve contrast according to the images or depths of ultrasound image signals subject to frequency decomposition, to improve contrast, particularly, at a deep area, and to prevent axial resolution degradation by applying 1D PSF estimation and restoration after frequency compounding.

The exemplary embodiment of the inventive concept may be implemented in the form of a storage medium that includes computer executable instructions, such as program modules, being executed by a computer. Computer-readable media may be any available media that may be accessed by the computer and includes volatile media such as a RAM, nonvolatile media such as a ROM, and removable and non-removable media. In addition, the computer-readable media may include computer storage media and communication media. Computer storage media includes the volatile media, non-volatile media, and removable and non-removable media implemented as any method or technology for storage of information such as computer readable instructions, data structures, program modules, or other data. The medium of communication is typically computer-readable instructions, and other data in a modulated data signal such as data structures, or program modules, or other transport mechanism and includes any information delivery media. Examples of the computer storage media include, for example, a ROM, a RAM, a flash memory, a compact disc (CD), a digital versatile disc (DVD), a magnetic disc, or a magnetic tape.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art.

What is claimed is:

1. An ultrasound imaging apparatus comprising:
    an ultrasound probe configured to receive echo ultrasonic waves reflected from an object, and to convert reflected echo ultrasonic waves into a first ultrasound image signal; and
    at least one processor configured to:
        analyze speckle noise of the first ultrasound image signal including a first portion and a second portion thereof,
        adjust a frequency band of the first portion of the first ultrasound image signal into a first frequency band, which is lower than the frequency band of the first portion, in response to the analyzed speckle noise of the first portion having a high speckle energy,
        adjust a frequency band of the second portion of the first ultrasound image signal into a second frequency band, which is higher than the frequency band of the second portion, in response to the analyzed speckle noise of the second portion having a low speckle energy,
        decompose the first ultrasound image signal, of which the frequency band of the first portion and the frequency band of the second portion have been adjusted, into one or more second ultrasound image signals of different frequency bands,
        compound the one or more second ultrasound image signals of the different frequency bands into a compounded third image signal, and
        restore an axial image based on the compounded third ultrasound image signal.

2. The ultrasound imaging apparatus according to claim 1, wherein the at least one processor is configured to analyze the speckle noise of the first ultrasound image signal according to a depth of the first ultrasound image signal.

3. The ultrasound imaging apparatus according to claim 1, wherein the at least one processor is configured to analyze speckle noise of the one or more second ultrasound image signals of the different frequency bands.

4. The ultrasound imaging apparatus according to claim 3, wherein the at least one processor is configured to adjust a frequency of the one or more second ultrasound image signals into the first frequency band in response to the speckle noise of the one or more second ultrasound image signals having the high speckle energy, or adjust the frequency of the one or more second ultrasound image signals into the second frequency band in response to the speckle noise of the one or more second ultrasound image signals having the low speckle energy.

5. The ultrasound imaging apparatus according to claim 1, wherein the at least one processor is configured to:
    obtain a speckle energy of the speckle noise of the first ultrasound image signal based on a difference between a pixel value of a speckle included in the first ultrasound image signal and a pixel value of an area adjacent to the speckle;
    compare the speckle energy of the speckle noise to a predetermined speckle energy; and
    determine that the speckle energy of the speckle noise is the high speckle energy based on the speckle energy being greater than the predetermined speckle energy or determine that the speckle energy of the speckle noise is the low speckle energy based on the speckle energy being lower than the predetermined speckle energy.

6. The ultrasound imaging apparatus according to claim 1, further comprising:
    a filter configured to pass the first portion of the first ultrasound image signal that has been adjusted into the first frequency band or pass the second portion of the first ultrasound image signal that has been adjusted into the second frequency band,
    wherein the at least one processor is configured to decompose the first ultrasound image signal into the one or more second ultrasound image signals of the different frequency bands based on the first portion or the second portion of the first ultrasound image signal passed by the filter.

7. The ultrasound imaging apparatus according to claim 1, wherein the at least one processor is configured to compound the one or more second ultrasound image signals of the different frequency bands, based on analysis of speckle noise of the one or more second ultrasound image signals of the different frequency bands.

8. The ultrasound imaging apparatus according to claim 1, wherein the at least one processor is configured to:
    estimate a point spread function (PSF) of the compounded third ultrasound image signal; and
    deconvolve the PSF estimated by the at least one processor with the compounded third ultrasound image signal to generate a restored image.

9. The ultrasound imaging apparatus according to claim 1, further comprising:
    a beamformer configured to convert analog signals into digital signals and vice versa and to adjust time differences between ultrasonic waves that are transmitted from or received by one or more transducers.

10. A method of controlling an ultrasound imaging apparatus comprising:
    analyzing speckle noise of a first ultrasound image signal including a first portion and a second portion thereof, the first ultrasound image signal being received from an ultrasound probe;
    adjusting a frequency band of the first portion of the first ultrasound image signal into a first frequency band, which is lower than the frequency band of the first portion, in response to the analyzed speckle noise of the first portion having a high speckle energy;
    adjusting a frequency band of the second portion of the first ultrasound image signal into a second frequency band, which is higher than the frequency band of the second portion, in response to the analyzed speckle noise of the second portion having a low speckle energy;
    decomposing the first ultrasound image signal, of which the frequency band of the first portion and the frequency band of the second portion have been adjusted, into one or more second ultrasound image signals of different frequency bands;
    compounding the one or more second ultrasound image signals of the different frequency bands; and
    outputting, to a display, a final image restored based on a result of the compounding.

11. The method according to claim 10, wherein the analyzing the speckle noise of the first ultrasound image signal comprises analyzing the speckle noise of the first ultrasound image signal according to a depth of the first ultrasound image signal.

12. The method according to claim 10, further comprising analyzing speckle noise of the one or more second ultrasound image signals of the different frequency bands.

13. The method according to claim 12, further comprising:

adjusting a frequency band of the one or more second ultrasound image signals into the first frequency band in response to the speckle noise of the one or more second ultrasound image signals having the high speckle energy, or adjusting the frequency band of the one or more second ultrasound image signals into the second frequency band in response to the speckle noise of the one or more second ultrasound image signals having the low speckle energy.

14. The method according to claim 10, further comprising:
passing the first portion of the first ultrasound image signal that has been adjusted into the first frequency band or passing the second portion of the first ultrasound image signal that has been adjusted into the second frequency band,
wherein the decomposing comprises decomposing the first ultrasound image signal into the one or more second ultrasound image signals of the different frequency bands based on the first portion or the second portion of the first ultrasound image signal passed in the passing.

15. An ultrasound imaging apparatus comprising:
an ultrasound probe configured to receive echo ultrasonic waves reflected from an object and to convert reflected echo ultrasonic waves into a first ultrasound image signal; and
an image processing apparatus comprising at least one processor and configured to:
analyze speckle noise of the first ultrasound image including a first portion and a second portion thereof,
adjust a frequency band of the first portion of the first ultrasound image signal into a first frequency band, which is lower than the frequency band of the first portion, in response to the analyzed speckle noise of the first portion having a high speckle energy,
adjust a frequency band of the second portion of the first ultrasound image signal into a second frequency band, which is higher than the frequency band of the second portion, in response to the analyzed speckle noise of the second portion having a low speckle energy,
decompose the first ultrasound image signal, of which the frequency band of the first portion and the frequency band of the second portion have been adjusted, into one or more second ultrasound image signals of different frequency bands,
compound the one or more second ultrasound images signals of the different frequency bands into a compounded third ultrasound image signal, and
restore an axial image based on the compounded third ultrasound image signal.

* * * * *